United States Patent
Fukumoto et al.

(10) Patent No.: US 9,044,013 B2
(45) Date of Patent: Jun. 2, 2015

(54) GLYOXIME DERIVATIVE AND PEST CONTROL AGENT

(71) Applicants: KUMIAI CHEMICAL INDUSTRY CO., LTD., Tokyo (JP); IHARA CHEMICAL INDUSTRY CO., LTD., Tokyo (JP)

(72) Inventors: Shunichirou Fukumoto, Shizuoka (JP); Daisuke Shikama, Shizuoka (JP); Toshihiro Nagata, Shizuoka (JP); Katsuya Kato, Shizuoka (JP); Kei Kawamoto, Shizuoka (JP); Masaaki Komatsu, Tokyo (JP); Takeshi Matsuda, Tokyo (JP); Seisuke Ito, Tokyo (JP)

(73) Assignees: KUMIAI CHEMICAL INDUSTRY CO., LTD., Tokyo (JP); IHARA CHEMICAL INDUSTRY CO., LTD., Tokyo (JP)

(*) Notice: Subject to any disclaimer, the term of this patent is extended or adjusted under 35 U.S.C. 154(b) by 0 days.

(21) Appl. No.: 14/360,527

(22) PCT Filed: Nov. 19, 2012

(86) PCT No.: PCT/JP2012/007400
§ 371 (c)(1),
(2) Date: May 23, 2014

(87) PCT Pub. No.: WO2013/080479
PCT Pub. Date: Jun. 6, 2013

(65) Prior Publication Data
US 2014/0288184 A1 Sep. 25, 2014

(30) Foreign Application Priority Data
Nov. 30, 2011 (JP) .................. 2011-261804

(51) Int. Cl.
| | | |
|---|---|---|
| *C07C 251/34* | (2006.01) | |
| *C07C 251/50* | (2006.01) | |
| *A01N 47/40* | (2006.01) | |
| *A01N 37/52* | (2006.01) | |
| *C07C 259/14* | (2006.01) | |
| *A01N 37/18* | (2006.01) | |

(52) U.S. Cl.
CPC .............. *A01N 37/52* (2013.01); *C07C 259/14* (2013.01); *C07C 2101/02* (2013.01); *C07C 2101/04* (2013.01); *C07C 2101/08* (2013.01); *C07C 2101/14* (2013.01); *A01N 37/18* (2013.01)

(58) Field of Classification Search
None
See application file for complete search history.

(56) References Cited

U.S. PATENT DOCUMENTS 5,773,624 A * 6/1998 Inagaki et al. ................ 548/128

FOREIGN PATENT DOCUMENTS

| CN | 102093266 A * | 6/2011 |
|---|---|---|
| DE | 4442732 A1 | 6/1996 |
| EP | 795551 A1 | 9/1997 |
| JP | 9-509656 A | 9/1997 |
| JP | 9-301965 A | 11/1997 |
| JP | 11-508248 A | 7/1999 |
| JP | 11-514658 A | 12/1999 |
| WO | 2011/161945 A1 | 12/2011 |

OTHER PUBLICATIONS

International Search Report (ISR) dated Jan. 15, 2013, for PCT/JP2012/007400, and English translation thereof.
Andrianov, V.G., "Synthesis and Properties of Derivatives of 4-Aminofuroxan-3-Carboxylic Acid", Chemistry of Heterocyclic Compounds, vol. 33, No. 8, 1997, pp. 973-976.
Arulsamy et al, "Nucleophilic Addition of Hydroxylamine, Methoxylamine, and Hydrazine to Malononitrileoxime", Journal of Organic Chemistry, 2000, vol. 65, No. 4, pp. 1139-1143.

* cited by examiner

*Primary Examiner* — Michael Barker
(74) *Attorney, Agent, or Firm* — Bacon & Thomas, PLLC

(57) ABSTRACT

The present invention provides a glyoxime derivative displaying excellent pesticidal effect or a salt thereof and a pesticide containing the same as an active ingredient. This pesticide is characterized by containing as an active ingredient, a glyoxime derivative expressed by the general formula [I] (in which X represents a cyano group or a carbamoyl group, $R^1$ represents a $C_1$~$C_8$ alkyl group, a $C_3$~$C_6$ cycloalkyl $C_1$~$C_6$ alkyl group, etc., and $R^2$ represents a hydrogen atom, a $C_1$~$C_8$ alkyl group, a $C_3$~$C_6$ cycloalkyl $C_1$~$C_6$ alkyl group, etc.) or an agriculturally acceptable salt thereof.

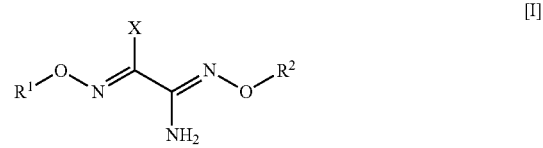

[I]

5 Claims, No Drawings

GLYOXIME DERIVATIVE AND PEST CONTROL AGENT

TECHNICAL FIELD

The present invention relates to a novel glyoxime derivative or a salt thereof, as well as to a pest control agent characterized by containing the derivative or salt thereof as an active ingredient.

BACKGROUND ART

For example, Patent Literature 1 is already known as a literature regarding compounds similar to the glyoxime derivative of the present invention.

Glyoxime derivatives are disclosed in the Patent Literature 1. However, they are restricted to those glyoxime derivatives in which the substituent on one oxygen is a sulfonyl group (e.g. methanesulfonyl group), and no glyoxime derivative according to the present invention is disclosed. Further in the literature, there is no disclosure on the control effect of the glyoxime derivatives on pests.

PRIOR ART LITERATURE

Patent Literature

Patent literature 1: EP-795551

SUMMARY OF THE INVENTION

Task to be Achieved by the Invention

It is desired that the pest control agents used for useful crops are applied to soil or foliage at a low chemical dose and yet exhibit a sufficient pest control effect. With the increasing requirements for the safety of chemical substances and the effect on environment, it is also desired to develop a safer pest control agent. Further, in recent years, the use over many years, of pest control agents (e.g. insecticides and miticides) have caused the appearance of pests resistant to these pest control agents, making difficult the complete control of pests. Also, the use of highly toxic pest control agents has caused problems regarding, for example, the safety to pest control agent operator.

Under such a situation, the task of the present invention is to solve the above-mentioned problems of conventional pest control agents and provide a pest control agent superior in safety, control effect, etc.

Means for Achieving the Task

In order to develop a pest control agent having the above-mentioned preferred properties, the present inventors synthesized various glyoxime derivatives and investigated their physiological activities. As a result, it was found that the glyoxime derivatives represented by the general formula [I] shown below show a control effect to pests and resistant pests and show a very high control (insecticidal) effect particularly to Hemipteran pests represented by *Nilaparvata lugens, Laodelphax striatella, Nephotettix cincticeps, Aphis gossypii*, etc. The finding has led to the completion of the present invention.

The present invention has a scope characterized as shown below (1) A pest control agent characterized by containing, as an active ingredient, a glyoxime derivative represented by the general formula [I]

[formula 1]

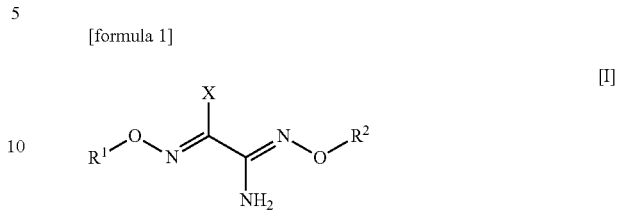

{in the formula,
X is a cyano group or a carbamoyl group,
$R^1$ is a $C_1 \sim C_8$ alkyl group, a $C_2 \sim C_6$ alkenyl group, a $C_2 \sim C_6$ alkynyl group, a $C_3 \sim C_6$ cycloalkyl group, a $C_3 \sim C_6$ cycloalkyl $C_1 \sim C_6$ alkyl group, a $C_1 \sim C_6$ haloalkyl group, a $C_1 \sim C_6$ alkoxy $C_1 \sim C_6$ alkyl group, a cyano $C_1 \sim C_6$ alkyl group or a phenyl $C_1 \sim C_6$ alkyl group which may be substituted by at least one substituent selected from the below-shown substituent group α, and
$R^2$ is a hydrogen atom, a $C_1 \sim C_8$ alkyl group, a $C_2 \sim C_6$ alkenyl group, a $C_2 \sim C_6$ alkynyl group, a $C_3 \sim C_6$ cycloalkyl group, a $C_3 \sim C_6$ cycloalkyl $C_1 \sim C_6$ alkyl group, a $C_1 \sim C_6$ haloalkyl group, a $C_1 \sim C_6$ alkoxy $C_1 \sim C_6$ alkyl group, a cyano $C_1 \sim C_6$ alkyl group or a phenyl $C_1 \sim C_6$ alkyl group which may be substituted by at least one substituent selected from the below-shown substituent group α,
[Substituent Group α]
a halogen atom, a $C_1 \sim C_6$ alkyl group, a $C_1 \sim C_6$ haloalkyl group, a $C_1 \sim C_6$ alkoxy group, a $C_1 \sim C_6$ haloalkoxy group, a nitro group or a cyano group},
or an agriculturally acceptable salt thereof.

(2) A glyoxime derivative represented by the general formula [I']

[formula 2]

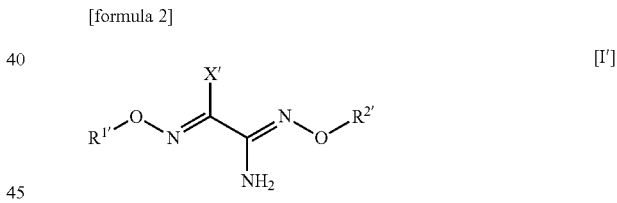

{in the formula,
X' is a cyano group or a carbamoyl group,
$R^{1'}$ is a $C_3 \sim C_8$ alkyl group, a $C_2 \sim C_6$ alkenyl group, a $C_2 \sim C_6$ alkynyl group, a $C_3 \sim C_6$ cycloalkyl group, a $C_3 \sim C_6$ cycloalkyl $C_1 \sim C_6$ alkyl group, a $C_2 \sim C_6$ haloalkyl group, a $C_1 \sim C_6$ alkoxy $C_1 \sim C_6$ alkyl group, a cyano $C_1 \sim C_6$ alkyl group or a phenyl $C_1 \sim C_6$ alkyl group which may be substituted by at least one substituent selected from the below-shown substituent group α, and
$R^{2'}$ is a hydrogen atom, a $C_1 \sim C_8$ alkyl group, a $C_2 \sim C_6$ alkenyl group, a $C_2 \sim C_6$ alkynyl group, a $C_3 \sim C_6$ cycloalkyl group, a $C_3 \sim C_6$ cycloalkyl $C_1 \sim C_6$ alkyl group, a $C_1 \sim C_6$ haloalkyl group, a $C_1 \sim C_6$ alkoxy $C_1 \sim C_6$ alkyl group, a cyano $C_1 \sim C_6$ alkyl group or a phenyl $C_1 \sim C_6$ alkyl group which may be substituted by at least one substituent selected from the below-shown substituent group α,
[Substituent Group α]
a halogen atom, a $C_1 \sim C_6$ alkyl group, a $C_1 \sim C_6$ haloalkyl group, a $C_1 \sim C_6$ alkoxy group, a $C_1 \sim C_6$ haloalkoxy group, a nitro group or a cyano group},
or an agriculturally acceptable salt thereof.

(3) A pest control agent according to (1), which is an insecticide.
(4) A method for pest control which uses the glyoxime derivative or agriculturally acceptable salt thereof, according to (2), at an effective amount.
(5) A method for pest control according to (4), which uses the glyoxime derivative or agriculturally acceptable salt thereof, as an insecticide.

Effect of the Invention

The present invention shows an excellent control effect to a variety of pests in agricultural and horticultural fields, can control even resistant pests, and are highly effective particularly to Hemipteran pests represented by *Nilaparvata lugens, Laodelphax striatella, Sogatella furcifera, Nephotettix cincticeps, Aphis gossypii, Bemisia tabaci*. etc.

DETAILED DESCRIPTION OF THE INVENTION

Explanation is made on the symbols and terms used in the present Description.

In the present invention, pest control agent means insecticides, miticides, nematicides, etc. used in agricultural and horticultural fields, animals (e.g. livestock and pets), households or disinfection.

In the present invention, halogen atom refers to a fluorine atom, a chlorine atom, a bromine atom or an iodine atom.

In the present invention, $C_1$~$C_6$ alkyl group refers to, unless otherwise specified, a straight chain or branched chain alkyl group of 1 to 6 carbon atoms. There can be mentioned, for example, methyl, ethyl, n-propyl, isopropyl, n-butyl, sec-butyl, isobutyl, tert-butyl, n-pentyl, 1-methylbutyl, 2-methylbutyl, isopentyl, 1-ethylpropyl, 1,1-dimethylpropyl, 1,2-dimethylpropyl, neopentyl, n-hexyl, 1-methylpentyl, 2-methylpentyl, 3-methylpentyl, isohexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, and 1-ethyl-1-methylpropyl groups.

In the present invention, $C_1$~$C_8$ alkyl group refers to, unless otherwise specified, a straight chain or branched chain alkyl group of 1 to 8 carbon atoms. There can be mentioned, for example, those groups mentioned for the $C_1$~$C_6$ alkyl group; and n-heptyl, 1-methylhexyl, 5-methylhexyl, 4,4-dimethylpentyl, n-octyl, 1-methylheptyl, 6-methylhexptyl and 5,5-dimethylhexyl groups.

In the present invention, $C_3$~$C_8$ alkyl group refers to, unless otherwise specified, a straight chain or branched chain alkyl group of 3 to 8 carbon atoms. There can be mentioned, for example, n-propyl, isopropyl, n-butyl, sec-butyl, isobutyl, tert-butyl, n-pentyl, 1-methylbutyl, 2-methylbutyl, isopentyl, 1-ethylpropyl, 1,1-dimethylpropyl, 1,2-dimethylpropyl, neopentyl, n-hexyl, 1-methylpentyl, 2-methylpentyl, 3-methylpentyl, isohexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl, n-heptyl, 1-methylhexyl, 5-methylhexyl, 4,4-dimethylpentyl, n-octyl, 1-methylheptyl, 6-methylheptyl and 5,5-dimethylhexyl groups.

In the present invention, $C_2$~$C_6$ alkenyl group refers to, unless otherwise specified, a straight chain or branched chain alkenyl group of 2 to 6 carbon atoms. There can be mentioned, for example, vinyl, 1-propenyl, isopropenyl, 2-propenyl, 1-butenyl, 1-methyl-1-propenyl, 2-butenyl, 1-methyl-2-propenyl, 3-butenyl, 2-methyl-1-propenyl, 2-methyl-2-propenyl, 1,3-butadienyl, 1-pentenyl, 1-ethyl-2-propenyl, 2-pentenyl, 1-methyl-1-butenyl, 3-pentenyl, 1-methyl-2-butenyl, 4-pentenyl, 1-methyl-3-butenyl, 3-methyl-1-butenyl, 1,2-dimethyl-2-propenyl, 1,1-dimethyl-2-propenyl, 2-methyl-2-butenyl, 3-methyl-2-butenyl, 1,2-dimethyl-1-propenyl, 2-methyl-3-butenyl, 3-methyl-3-butenyl, 1,3-pentadienyl, 1,3-butadien-2-yl, 1-hexenyl, 1-propyl-2-propenyl, 2-hexenyl, 1-methyl-1-pentenyl, 1-ethyl-2-butenyl, 3-hexenyl, 4-hexenyl, 5-hexenyl, 1-methyl-4-pentenyl, 1-ethyl-3-butenyl, 4-methyl-1-penten-2-yl, 1-ethyl-1-methyl-2-propenyl, 1-ethyl-2-methyl-2-propenyl, 4-methyl-1-penten-3-yl, 2-methyl-2-pentenyl, 3-methyl-3-pentenyl, 4-methyl-3-pentenyl, 1,3-dimethyl-2-butenyl, 1,1-dimethyl-3-butenyl, 3-methyl-4-pentenyl, 4-methyl-4-pentenyl, 1,2-dimethyl-3-butenyl, 1,3-dimethyl-3-butenyl, 1,1,2-trimethyl-2-propenyl, 1,5-hexadienyl, 1,4-pentadien-2-yl, and 2,4-hexadienyl groups.

In the present invention, $C_2$~$C_6$ alkynyl group refers to, unless otherwise specified, a straight chain or branched chain alkynyl group of 2 to 6 carbon atoms. There can be mentioned, for example, ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 1-(n-propyl)-2-propynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, 1-ethyl-3-butynyl, 1-ethyl-1-methyl-2-propynyl, 4-methyl-1-pentyn-3-yl, 1,1-dimethyl-2-butynyl and 2,2-dimethyl-3-butynyl groups.

In the present invention, $C_3$~$C_6$ cycloalkyl group refers to, unless otherwise specified, a cycloalkyl group of 3 to 6 carbon atoms. There can be mentioned, for example, cyclopropyl, cyclobutyl, cyclopentyl and cyclohexyl groups.

In the present invention, $C_3$~$C_6$ cycloalkyl $C_1$~$C_6$ alkyl group refers to, unless otherwise specified, a ($C_3$~$C_6$ cycloalkyl)-($C_1$~$C_6$ alkyl) group wherein the cycloalkyl moiety and the alkyl moiety have each the above-mentioned meaning. There can be mentioned, for example, cyclopropylmethyl, cyclobutylmethyl, cyclopentylmethyl and cyclohexylmethyl groups.

In the present invention, $C_1$~$C_6$ alkoxy group refers to, unless otherwise specified, a ($C_1$~$C_6$ alkyl)-O-group wherein the alkyl moiety has the above-mentioned meaning. There can be mentioned, for example, methoxy, ethoxy, n-propoxy, isopropxy, n-butoxy, isobutoxy, tert-butoxy, pentyloxy, isopentyloxy, hexyloxy and isohexyloxy groups.

In the present invention, $C_1$~$C_6$ haloalkyl group refers to, unless otherwise specified, a straight chain or branched chain alkyl group of 1 to 6 carbon atoms, substituted with 1 to 13, preferably 1 to 5 same or different halogen atoms. There can be mentioned, for example, difluoromethyl, 2-fluoroethyl, 2,2-difluoroethyl, 2,2,2-trifluoroethyl, 2,2,2-trichloroethyl, 3,3,3-trifluoropropyl, 2,2,3,3,3-pentafluoropropyl and 1,1,2,3,3,3-hexafluoropropyl groups.

In the present invention, $C_2$~$C_6$ haloalkyl group refers to, unless otherwise specified, a straight chain or branched chain alkyl group of 2 to 6 carbon atoms, substituted with 1 to 13, preferably 1 to 5 same or different halogen atoms. There can be mentioned, for example, 2-fluoroethyl, 2,2-difluoroethyl, 2,2,2-trifluoroethyl, 2,2,2-trichloroethyl, 3,3,3-trifluoropropyl, 2,2,3,3,3-pentafluoropropyl and 1,1,2,3,3,3-hexafluoropropyl groups.

In the present invention, $C_1$~$C_6$ haloalkoxy group refers to, unless otherwise specified, a ($C_1$~$C_6$ haloalkyl)-O-group wherein the haloalkyl moiety has the above-mentioned meaning. There can be mentioned, for example, chloromethoxy, difluoromethoxy, chlorodifluoromethoxy, trifluoromethoxy, 2,2-difluoroethoxy and 2,2,2-trifluoroethoxy groups.

In the present invention, $C_1 \sim C_6$ alkoxy $C_1 \sim C_6$ alkyl group refers to, unless otherwise specified, a $(C_1 \sim C_6$ alkoxy)-$(C_1 \sim C_6$ alkyl)-group, wherein the alkyl moiety and the alkoxy moiety have each the above-mentioned meaning.

There can be mentioned, for example, methoxymethyl, ethoxymethyl, isopropoxymethyl, pentyloxymethyl, 2-methoxyethyl, 2-ethoxyethyl and 2-butoxyethyl groups.

In the present invention, phenyl $C_1 \sim C_6$ alkyl group refers to, unless otherwise specified, an alkyl group of 1 to 6 carbon atoms, substituted with phenyl group, wherein the alkyl moiety has the above-mentioned meaning. There can be mentioned, for example, benzyl, 1-phenylethyl and 2-phenylethyl groups.

Incidentally, the phenyl $C_1 \sim C_6$ alkyl group may be substituted with at least one substituent selected from the substituent group α.

In the present invention, cyano $C_1 \sim C_6$ alkyl group refers to, unless otherwise specified, an alkyl group of 1 to 6 carbon atoms, substituted with cyano group, wherein the alkyl moiety has the above-mentioned meaning. There can be mentioned, for example, cyanomethyl group and 1-cyanobutyl group.

As the compounds included in the glyoxime derivative of general formula [I] and the glyoxime derivative of general formula [I'], there can be mentioned those compounds in which the above-mentioned substituents are combined. However, the following compounds are preferred in view of their pesticidal effects.

Compounds in which X or X' is a cyano group, $R^1$ or $R^{1'}$ is an n-propyl group, an isopropyl group or an n-butyl group, and $R^2$ or $R^{2'}$ is hydrogen, an n-propyl, or an isopropyl group.

Compounds in which X or X' is a carbamoyl group, $R^1$ or $R^{1'}$ is an n-propyl group or an isopropyl group, and $R^2$ or $R^{2'}$ is hydrogen, an n-propyl group or an isopropyl group.

Compounds in which X or X' is a cyano group, $R^1$ or $R^{1'}$ is a 2-propynil group or a 2-propenyl group, and $R^2$ or $R^{2'}$ is an n-propyl group or an isopropyl group.

The agriculturally acceptable salt refers to a salt of any compound included in the glyoxime derivative of the above general formula, of the present invention, and containing hydroxyl group, amino group or the like in the structure, with a metal or an organic base, or with a mineral acid or an organic acid. As the metal, there can be mentioned alkali metals (e.g. sodium and potassium) and alkaline earth metals (e.g. magnesium and calcium). As the organic base, there can be mentioned, for example, triethylamine and diisopropylamine. As the mineral acid, there can be mentioned, for example, hydrochloric acid hydrobromic acid and sulfuric acid. As the organic acid, there can be mentioned, for example, formic acid, acetic acid, methanesulfonic acid, 4-toluenesulfonic acid and trifluoromethanesulfonic acid.

Next, representative examples of the compounds included in the glyoxime derivative of the above general formula, of the present invention, are shown in Tables 1 to 12. However, the compounds included in present invention is not restricted thereto. The No. of each compound shown in each Table is referred to in the later description.

Incidentally, the compounds included in the present glyoxime derivative contain, in some cases, geometrical isomers of E-form and Z-form, depending upon the kinds of substituents. The present invention includes the E-isomers, the Z-isomers, and the mixtures of any mixing ratio of E-isomer and Z-isomer.

In the present Description, the following expressions in Tables refer to corresponding groups.

Me: methyl group
Et: ethyl group
Pr-n: n-propyl group
Pr-i: isopropyl group
Pr-c: cyclopropyl group
Bu-n: n-butyl group
Bu-s: sec-butyl group
Bu-i: isobutyl group
Bu-t: tert-butyl group
Pen-n: n-pentyl group
Pen-c: cyclopentyl group
Pen-i: isopentyl group
Pen-neo: neopentyl group
Pen-2: 1-methylbutyl group
Pen-3: 1-ethylpropyl group
Hex-n: n-hexyl group
Hex-c: cyclohexyl group Also, for example, the following expressions have corresponding meanings.

5-$CF_3$: substituted with trifluoromethyl group at 5-position
3-Cl-5-$CF_3$: substituted with chlorine atom at 3-position and with trifluoromethyl group at 5-position
2,6-$(Cl)_2$: substituted with chlorine atom at 2- and 6-positions

TABLE 1

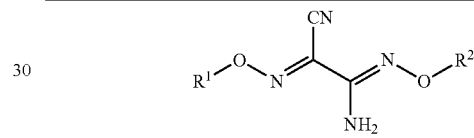

| Compond No. | $R^1$ | $R^2$ |
|---|---|---|
| 1-001 | Me | H |
| 1-002 | Et | H |
| 1-003 | Pr-n | H |
| 1-004 | Pr-i | H |
| 1-005 | Bu-n | H |
| 1-006 | Bu-i | H |
| 1-007 | Bu-s | H |
| 1-008 | Bu-t | H |
| 1-009 | Pen-n | H |
| 1-010 | Pen-i | H |
| 1-011 | Pen-neo | H |
| 1-012 | Pen-2 | H |
| 1-013 | Pen-3 | H |
| 1-014 | Hex-n | H |
| 1-015 | $CH_2CH_2C(Me)_3$ | H |
| 1-016 | Pen-c | H |
| 1-017 | Hex-c | H |
| 1-018 | $CH_2$Pr-c | H |
| 1-019 | $CH_2$Bu-c | H |
| 1-020 | $CH_2$Pen-c | H |
| 1-021 | $CH_2CH{=}CH_2$ | H |
| 1-022 | $CH_2C{\equiv}CH$ | H |
| 1-023 | $CH_2C{\equiv}CCH_3$ | H |
| 1-024 | Me | Me |
| 1-025 | Et | Me |

TABLE 2

| Compond No. | $R^1$ | $R^2$ |
|---|---|---|
| 1-026 | Pr-n | Me |
| 1-027 | Pr-i | Me |
| 1-028 | Bu-n | Me |
| 1-029 | Bu-i | Me |
| 1-030 | Bu-s | Me |

TABLE 2-continued

| Compond No. | R¹ | R² |
|---|---|---|
| 1-031 | Bu-t | Me |
| 1-032 | Pen-n | Me |
| 1-033 | Pen-i | Me |
| 1-034 | Pen-neo | Me |
| 1-035 | Pen-2 | Me |
| 1-036 | Pen-3 | Me |
| 1-037 | Hex-n | Me |
| 1-038 | $CH_2CH_2C(Me)_3$ | Me |
| 1-039 | Pen-c | Me |
| 1-040 | Hex-c | Me |
| 1-041 | $CH_2Pr$-c | Me |
| 1-042 | $CH_2Bu$-c | Me |
| 1-043 | $CH_2Pen$-c | Me |
| 1-044 | $CH_2CH{=}CH_2$ | Me |
| 1-045 | $CH_2C{\equiv}CH$ | Me |
| 1-046 | $CH_2C{\equiv}CCH_3$ | Me |
| 1-047 | Me | Et |
| 1-048 | Et | Et |
| 1-049 | Pr-n | Et |
| 1-050 | Pr-i | Et |
| 1-051 | Bu-n | Et |
| 1-052 | Bu-i | Et |
| 1-053 | Bu-s | Et |
| 1-054 | Bu-t | Et |

TABLE 3

| Compond No. | R¹ | R² |
|---|---|---|
| 1-055 | Pen-n | Et |
| 1-056 | Pen-i | Et |
| 1-057 | Pen-neo | Et |
| 1-058 | Pen-2 | Et |
| 1-059 | Pen-3 | Et |
| 1-060 | Hex-n | Et |
| 1-061 | $CH_2CH_2C(Me)_3$ | Et |
| 1-062 | Pen-c | Et |
| 1-063 | Hex-c | Et |
| 1-064 | $CH_2Pr$-c | Et |
| 1-065 | $CH_2Bu$-c | Et |
| 1-066 | $CH_2Pen$-c | Et |
| 1-067 | $CH_2CH{=}CH_2$ | Et |
| 1-068 | $CH_2C{\equiv}CH$ | Et |
| 1-069 | $CH_2C{\equiv}CCH_3$ | Et |
| 1-070 | Me | Pr-n |
| 1-071 | Et | Pr-n |
| 1-072 | Pr-n | Pr-n |
| 1-073 | Pr-i | Pr-n |
| 1-074 | Bu-n | Pr-n |
| 1-075 | Bu-i | Pr-n |
| 1-076 | Bu-s | Pr-n |
| 1-077 | Bu-t | Pr-n |
| 1-078 | Pen-n | Pr-n |
| 1-079 | Pen-i | Pr-n |
| 1-080 | Pen-neo | Pr-n |
| 1-081 | Pen-2 | Pr-n |
| 1-082 | Pen-3 | Pr-n |
| 1-083 | Hex-n | Pr-n |

TABLE 4

| Compond No. | R¹ | R² |
|---|---|---|
| 1-084 | $CH_2C(Me)_3$ | Pr-n |
| 1-085 | Pen-c | Pr-n |
| 1-086 | Hex-c | Pr-n |
| 1-087 | $CH_2Pr$-c | Pr-n |
| 1-088 | $CH_2Bu$-c | Pr-n |
| 1-089 | $CH_2Pen$-c | Pr-n |
| 1-090 | $CH_2CH{=}CH_2$ | Pr-n |

TABLE 4-continued

| Compond No. | R¹ | R² |
|---|---|---|
| 1-091 | $CH_2C{\equiv}CH$ | Pr-n |
| 1-092 | $CH_2C{\equiv}CCH_3$ | Pr-n |
| 1-093 | Me | Pr-i |
| 1-094 | Et | Pr-i |
| 1-095 | Pr-n | Pr-i |
| 1-096 | Pr-i | Pr-i |
| 1-097 | Bu-n | Pr-i |
| 1-098 | Bu-i | Pr-i |
| 1-099 | Bu-s | Pr-i |
| 1-100 | Bu-t | Pr-i |
| 1-101 | Pen-n | Pr-i |
| 1-102 | Pen-i | Pr-i |
| 1-103 | Pen-neo | Pr-i |
| 1-104 | Pen-2 | Pr-i |
| 1-105 | Pen-3 | Pr-i |
| 1-106 | Hex-n | Pr-i |
| 1-107 | $CH_2CH_2C(Me)_3$ | Pr-i |
| 1-108 | Pen-c | Pr-i |
| 1-109 | Hex-c | Pr-i |
| 1-110 | $CH_2Pr$-c | Pr-i |
| 1-111 | $CH_2Bu$-c | Pr-i |
| 1-112 | $CH_2Pen$-c | Pr-i |

TABLE 5

| Compond No. | R¹ | R² |
|---|---|---|
| 1-113 | $CH_2CH{=}CH_2$ | Pr-i |
| 1-114 | $CH_2C{\equiv}CH$ | Pr-i |
| 1-115 | $CH_2C{\equiv}CCH_3$ | Pr-i |
| 1-116 | Pr-i | Bu-i |
| 1-117 | Pr-i | Pen-i |
| 1-118 | Pr-i | $CH_2Pr$-c |
| 1-119 | Pr-i | $CH_2CF_3$ |
| 1-120 | Pr-i | $CH_2CH_2OCH_2CH_3$ |
| 1-121 | Pr-i | $CH_2CH{=}CH_2$ |
| 1-122 | Pr-i | $CH_2C{\equiv}CH$ |
| 1-123 | Pr-i | Bu-t |
| 1-124 | Pr-i | Bu-s |
| 1-125 | Pr-i | $CH_2CN$ |
| 1-126 | Pr-i | $CH_2C{\equiv}CCH_3$ |
| 1-127 | Pr-i | Pen-3 |
| 1-128 | Pr-i | Pen-2 |
| 1-129 | Me | Bu-i |
| 1-130 | Me | Pen-i |
| 1-131 | Me | $CH_2Ph$ |
| 1-132 | Me | $CH_2CH_2OCH_2CH_3$ |
| 1-133 | Me | $CH_2Pr$-c |
| 1-134 | Me | Pen-c |
| 1-135 | $CH_2Pr$-c | $CH_2Pr$-c |
| 1-136 | $CH_2Pr$-c | $CF_2CHFCF_3$ |
| 1-137 | $CH_2Pr$-c | $CHF_2$ |
| 1-138 | $CH_2CF_3$ | H |
| 1-139 | $CH_2CF_3$ | Pr-n |
| 1-140 | $CH_2(CH_2)_6CH_3$ | H |
| 1-141 | $CH_2Ph$ | H |

TABLE 6

| Compond No. | R¹ | R² |
|---|---|---|
| 1-142 | $CH_2Ph$ | $CH_2CF_3$ |
| 1-143 | $CH_2Ph$ | Me |
| 1-144 | $CH_2Ph$ | $CH_2CF_2CF_3$ |
| 1-145 | $CH_2Ph(3\text{-}CN)$ | $CH_2CF_2CF_3$ |
| 1-146 | $CH_2Ph(3\text{-}NO_2)$ | $CH_2CF_2CF_3$ |
| 1-147 | $CH_2Ph$ | Et |
| 1-148 | $CH_2Ph$ | Pr-n |
| 1-149 | $CH_2Ph$ | Bu-n |
| 1-150 | $CH_2Ph(2,6\text{-}CH_3)$ | $CH_2CH{=}CH_2$ |

TABLE 6-continued

| Compond No. | R¹ | R² |
|---|---|---|
| 1-151 | $CH_2Ph(3\text{-}OCF_3)$ | $CH_2CH=CH_2$ |
| 1-152 | $CH_2CH_2OCH_2CH_3$ | $CH_2CH=CH_2$ |
| 1-153 | $CH_2CN$ | $CH_2CH=CH_2$ |
| 1-154 | $CH_2CH=CHCH_3$ | H |
| 1-155 | $CH_2CH=CHCH_3$ | Pr-n |
| 1-156 | $CH_2CH=CH_2$ | Bu-n |
| 1-157 | $CH_2CH=CH_2$ | Pen-n |
| 1-158 | $CH_2CH=CH_2$ | Hex-n |
| 1-159 | $CH_2CH=CH_2$ | $CH_2Ph$ |
| 1-160 | $CH_2C{\equiv}CH$ | Bu-n |
| 1-161 | $CH_2C{\equiv}CH$ | $CH_2Ph$ |
| 1-162 | $CH_2CF_2CF_3$ | Pr-n |
| 1-163 | $CH_2CF_2CF_3$ | Pr-i |
| 1-164 | $CH_2Ph(4\text{-}OCH_3)$ | $CH_2CF_3$ |
| 1-165 | $CH_2Ph(4\text{-}Cl)$ | $CH_2CF_3$ |
| 1-166 | $CH_2Ph(2,6\text{-}Cl_2)$ | $CH_2CF_3$ |
| 1-167 | $CH_2Ph(3\text{-}CF_3)$ | $CH_2CF_3$ |
| 1-168 | $CH_2CF_3$ | $CH_2CF_3$ |

TABLE 7

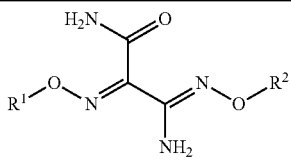

| Compond No. | R¹ | R² |
|---|---|---|
| 2-001 | Me | H |
| 2-002 | Et | H |
| 2-003 | Pr-n | H |
| 2-004 | Pr-i | H |
| 2-005 | Bu-n | H |
| 2-006 | Bu-i | H |
| 2-007 | Bu-s | H |
| 2-008 | Bu-t | H |
| 2-009 | Pen-n | H |
| 2-010 | Pen-i | H |
| 2-011 | Pen-neo | H |
| 2-012 | Pen-2 | H |
| 2-013 | Pen-3 | H |
| 2-014 | Hex-n | H |
| 2-015 | $CH_2CH_2C(Me)_3$ | H |
| 2-016 | Pen-c | H |
| 2-017 | Hex-c | H |
| 2-018 | $CH_2Pr\text{-}c$ | H |
| 2-019 | $CH_2Bu\text{-}c$ | H |
| 2-020 | $CH_2Pen\text{-}c$ | H |
| 2-021 | $CH_2CH=CH_2$ | H |
| 2-022 | $CH_2C{\equiv}CH$ | H |
| 2-023 | $CH_2C{\equiv}CCH_3$ | H |
| 2-024 | Me | Me |
| 2-025 | Et | Me |

TABLE 8

| Compond No. | R¹ | R² |
|---|---|---|
| 2-026 | Pr-n | Me |
| 2-027 | Pr-i | Me |
| 2-028 | Bu-n | Me |
| 2-029 | Bu-i | Me |
| 2-030 | Bu-s | Me |
| 2-031 | Bu-t | Me |
| 2-032 | Pen-n | Me |
| 2-033 | Pen-i | Me |
| 2-034 | Pen-neo | Me |

TABLE 8-continued

| Compond No. | R¹ | R² |
|---|---|---|
| 2-035 | Pen-2 | Me |
| 2-036 | Pen-3 | Me |
| 2-037 | Hex-n | Me |
| 2-038 | $CH_2CH_2C(Me)_3$ | Me |
| 2-039 | Pen-c | Me |
| 2-040 | Hex-c | Me |
| 2-041 | $CH_2Pr\text{-}c$ | Me |
| 2-042 | $CH_2Bu\text{-}c$ | Me |
| 2-043 | $CH_2Pen\text{-}c$ | Me |
| 2-044 | $CH_2CH=CH_2$ | Me |
| 2-045 | $CH_2C{\equiv}CH$ | Me |
| 2-046 | $CH_2C{\equiv}CCH_3$ | Me |
| 2-047 | Me | Et |
| 2-048 | Et | Et |
| 2-049 | Pr-n | Et |
| 2-050 | Pr-i | Et |
| 2-051 | Bu-n | Et |
| 2-052 | Bu-i | Et |
| 2-053 | Bu-s | Et |
| 2-054 | Bu-t | Et |

TABLE 9

| Compond No. | R¹ | R² |
|---|---|---|
| 2-055 | Pen-n | Et |
| 2-056 | Pen-i | Et |
| 2-057 | Pen-neo | Et |
| 2-058 | Pen-2 | Et |
| 2-059 | Pen-3 | Et |
| 2-060 | Hex-n | Et |
| 2-061 | $CH_2CH_2C(Me)_3$ | Et |
| 2-062 | Pen-c | Et |
| 2-063 | Hex-c | Et |
| 2-064 | $CH_2Pr\text{-}c$ | Et |
| 2-065 | $CH_2Bu\text{-}c$ | Et |
| 2-066 | $CH_2Pen\text{-}c$ | Et |
| 2-067 | $CH_2CH=CH_2$ | Et |
| 2-068 | $CH_2C{\equiv}CH$ | Et |
| 2-069 | $CH_2C{\equiv}CCH_3$ | Et |
| 2-070 | Me | Pr-n |
| 2-071 | Et | Pr-n |
| 2-072 | Pr-n | Pr-n |
| 2-073 | Pr-i | Pr-n |
| 2-074 | Bu-n | Pr-n |
| 2-075 | Bu-i | Pr-n |
| 2-076 | Bu-s | Pr-n |
| 2-077 | Bu-t | Pr-n |
| 2-078 | Pen-n | Pr-n |
| 2-079 | Pen-i | Pr-n |
| 2-080 | Pen-neo | Pr-n |
| 2-081 | Pen-2 | Pr-n |
| 2-082 | Pen-3 | Pr-n |
| 2-083 | Hex-n | Pr-n |

TABLE 10

| Compond No. | R¹ | R² |
|---|---|---|
| 2-084 | $CH_2CH_2C(Me)_3$ | Pr-n |
| 2-085 | Pen-c | Pr-n |
| 2-086 | Hex-c | Pr-n |
| 2-087 | $CH_2Pr\text{-}c$ | Pr-n |
| 2-088 | $CH_2Bu\text{-}c$ | Pr-n |
| 2-089 | $CH_2Pen\text{-}c$ | Pr-n |
| 2-090 | $CH_2CH=CH_2$ | Pr-n |
| 2-091 | $CH_2C{\equiv}CH$ | Pr-n |
| 2-092 | $CH_2C{\equiv}CCH_3$ | Pr-n |
| 2-093 | Me | Pr-i |
| 2-094 | Et | Pr-i |

TABLE 10-continued

| Compond No. | R¹ | R² |
|---|---|---|
| 2-095 | Pr-n | Pr-i |
| 2-096 | Pr-i | Pr-i |
| 2-097 | Bu-n | Pr-i |
| 2-098 | Bu-i | Pr-i |
| 2-099 | Bu-s | Pr-i |
| 2-100 | Bu-t | Pr-i |
| 2-101 | Pen-n | Pr-i |
| 2-102 | Pen-i | Pr-i |
| 2-103 | Pen-neo | Pr-i |
| 2-104 | Pen-2 | Pr-i |
| 2-105 | Pen-3 | Pr-i |
| 2-106 | Hex-n | Pr-i |
| 2-107 | $CH_2CH_2C(Me)_3$ | Pr-i |
| 2-108 | Pen-c | Pr-i |
| 2-109 | Hex-c | Pr-i |
| 2-110 | $CH_2Pr$-c | Pr-i |
| 2-111 | $CH_2Bu$-c | Pr-i |
| 2-112 | $CH_2Pen$-c | Pr-i |

TABLE 11

| Compond No. | R¹ | R² |
|---|---|---|
| 2-113 | $CH_2CH=CH_2$ | Pr-i |
| 2-114 | $CH_2C≡CH$ | Pr-i |
| 2-115 | $CH_2C≡CCH_3$ | Pr-i |
| 2-116 | Pr-i | Bu-i |
| 2-117 | Pr-i | Pen-i |
| 2-118 | Pr-i | $CH_2Pr$-c |
| 2-119 | Pr-i | $CH_2CF_3$ |
| 2-120 | Pr-i | $CH_2CH_2OCH_2CH_3$ |
| 2-121 | Pr-i | $CH_2C≡CH$ |
| 2-122 | Pr-i | $CH_2C≡CCH_3$ |
| 2-123 | Pr-i | Bu-t |
| 2-124 | Pr-i | Bu-s |
| 2-125 | Pr-i | $CH_2CN$ |
| 2-126 | Pr-i | $CH_2C≡CCH_3$ |
| 2-127 | Pr-i | Pen-3 |
| 2-128 | Pr-i | Pen-2 |
| 2-129 | Me | Bu-i |
| 2-130 | Me | Pen-i |
| 2-131 | Me | $CH_2Ph$ |
| 2-132 | Me | $CH_2CH_2OCH_2CH_3$ |
| 2-133 | Me | $CH_2Pen$-c |
| 2-134 | Me | Pen-c |
| 2-135 | $CH_2Pr$-c | $CH_2Pr$-c |
| 2-136 | $CH_2Pr$-c | $CF_2CHFCF_3$ |
| 2-137 | $CH_2Pr$-c | $CHF_2$ |
| 2-138 | $CH_2CF_3$ | H |
| 2-139 | $CH_2CF_3$ | Pr-n |
| 2-140 | $CH_2(CH_2)_6CH_3$ | H |
| 2-141 | $CH_2Ph$ | H |

TABLE 12

| Compond No. | R¹ | R² |
|---|---|---|
| 2-142 | $CH_2Ph$ | $CH_2CF_3$ |
| 2-143 | $CH_2Ph$ | Me |
| 2-144 | $CH_2Ph$ | $CH_2CF_2CF_3$ |
| 2-145 | $CH_2Ph(3$-CN$)$ | $CH_2CF_2CF_3$ |
| 2-146 | $CH_2Ph(3$-NO$_2)$ | $CH_2CF_2CF_3$ |
| 2-147 | $CH_2Ph$ | Et |
| 2-148 | $CH_2Ph$ | Pr-n |
| 2-149 | $CH_2Ph$ | Bu-n |
| 2-150 | $CH_2Ph(2,6$-CH$_3)$ | $CH_2CH=CH_2$ |
| 2-151 | $CH_2Ph(3$-OCF$_3)$ | $CH_2CH=CH_2$ |
| 2-152 | $CH_2CH_2OCH_2CH_3$ | $CH_2CH=CH_2$ |
| 2-153 | $CH_2CN$ | $CH_2CH=CH_2$ |
| 2-154 | $CH_2CH=CHCH_3$ | H |

TABLE 12-continued

| Compond No. | R¹ | R² |
|---|---|---|
| 2-155 | $CH_2CH=CHCH_3$ | Pr-n |
| 2-156 | $CH_2CH=CH_2$ | Bu-n |
| 2-157 | $CH_2CH=CH_2$ | Pen-n |
| 2-158 | $CH_2CH=CH_2$ | Hex-n |
| 2-159 | $CH_2CH=CH_2$ | $CH_2Ph$ |
| 2-160 | $CH_2C≡CH$ | Bu-n |
| 2-161 | $CH_2C≡CH$ | $CH_2Ph$ |
| 2-162 | $CH_2CF_2CF_3$ | Pr-n |
| 2-163 | $CH_2CF_2CF_3$ | Pr-i |
| 2-164 | $CH_2Ph(4$-OCH$_3)$ | $CH_2CF_3$ |
| 2-165 | $CH_2Ph(4$-Cl$)$ | $CH_2CF_3$ |
| 2-166 | $CH_2Ph(2,6$-Cl$_2)$ | $CH_2CF_3$ |
| 2-167 | $CH_2Ph(3$-CF$_3)$ | $CH_2CF_3$ |
| 2-168 | $CH_2CF_3$ | $CH_2CF_3$ |

The glyoxime derivative represented by the general formula, of the present invention can be produced by the production methods shown below. However, the production is not restricted by these methods.

In the following, for example, "compound represented by the general formula [II]", "compound represented by formula [II]" and "compound [II]" have the same meaning.

[Production Method 1]

Of the glyoxime derivatives represented by the general formula, the compound represented by the general formula [VI] can be produced, for example, by the following method.

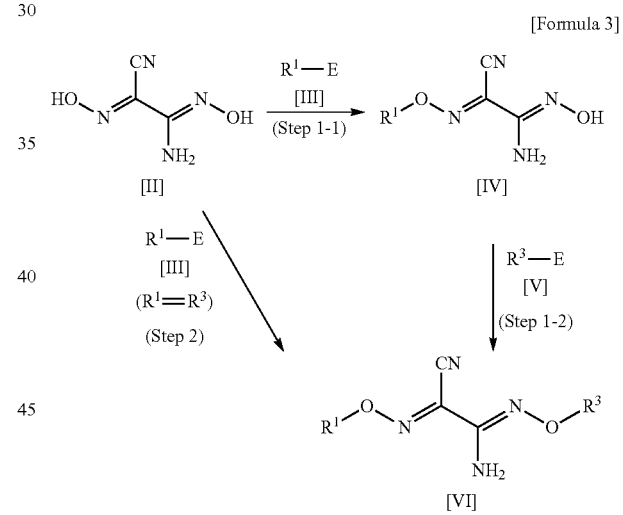

[Formula 3]

(In the formula, $R^1$ has the same meaning as given above; $R^3$ is a $C_1$~$C_8$ alkyl group, a $C_2$~$C_6$ alkenyl group, a $C_2$~$C_6$ alkynyl group, a $C_3$~$C_6$ cycloalkyl group, a $C_3$~$C_6$ cycloalkyl $C_1$~$C_6$ alkyl group, a $C_1$~$C_6$ haloalkyl group, a $C_1$~$C_6$ alkoxy $C_1$~$C_6$ alkyl group, a cyano $C_1$~$C_6$ alkyl group, or a phenyl $C_1$~$C_6$ alkyl group which may be substituted with at least one substituent selected from the substituent group α; and E is a leaving group such as chlorine atom, bromine atom, iodine atom, methanesulfonyl group, methanesulfonyloxy group, trifluoromethanesulfonyloxy group or the like).

(Step 1-1)

The compound [IV] can be produced by reacting a compound [II] with a compound [III] in an appropriate solvent in the presence of an appropriate base. Incidentally, the compound [II] can be produced based on the method described in Journal of Organic Chemistry, 2000, Vol 65, No. 4, pp. 1139-1143.

The amount of the compound [III] used in the reaction is appropriately selected ordinarily in a range of 1 to 5 equivalents relative to 1 equivalent of the compound [II] and is preferably 1 to 2 equivalents.

As the solvent usable in the reaction, there ca be mentioned, for example, ethers such as diethyl ether, 1,2-dimethoxyethane, tetrahydrofuran and the like; amides such as N,N-dimethylacetamide, N,N-dimethylformamide, 1,3-dimethyl-2-imidazolidinone, N-methyl-2-pyrrolidinone and the like; sulfur compounds such as dimethyl sulfoxide, sulfolane and the like; nitriles such as acetonitrile, propionitrile and the like; aliphatic hydrocarbons such as hexane, heptane and the like; aromatic hydrocarbons such as benzene, toluene, xylene and the like; halogenated hydrocarbons such as 1,2-dichloroethane, chlorobenzene and the like; water, and mixed solvents thereof. The use amount of the solvent is ordinarily 0.1 to 50 liters, preferably 0.2 to 3.0 liters relative to 1 mol of the compound [II].

As the base usable in the reaction, there can be mentioned, for example, inorganic bases such as alkali metal hydroxides (e.g. sodium hydroxide and potassium hydroxyide), alkali metal carbonates (e.g. sodium carbonate and potassium carbonate), alkali metal bicarbonates (e.g. sodium hydrogencarbonate and potassium hydrogencarbonate) and the like; metal hydrides such as sodium hydride, potassium hydride and the like; and organic bases such as triethylamine, 1,8-diazabicyclo[5.4.0]-7-undecene and the like. The use amount of the base is appropriately selected ordinarily in a range of 1 to 10 equivalents relative to 1 equivalent of the compound [II] and is preferably 1 to 5 equivalents.

The reaction temperature of the reaction is ordinarily any temperature from −20° C. to the reflux temperature of the reaction system and is preferably −10° C. to 100° C.

The reaction time of the reaction differs depending upon the reaction temperature, the substrate of reaction, the amount of reaction, etc., but is ordinarily 1 to 48 hours.

After the completion of the reaction, there are conducted operations such as poring of water into reaction mixture, extraction with organic solvent, concentration and the like, whereby the compound [IV] can be isolated. The isolated compound [IV] can be purified as necessary by column chromatography, recrystallization, etc.

(Step 1-2)

The compound [VI] can be produced by reacting the compound [IV] with a compound [V] in an appropriate solvent in the presence of an appropriate base.

The amount of the compound [V] used in the reaction is appropriately selected ordinarily in a range of 1 to 5 eluivalents relative to 1 equivalent of the compound [IV] and is preferably 1 to 2 equivalents.

As the solvent and base usable in the reaction, there can be mentioned the same solvents and bases as mentioned in the (step 1-1). The use amount of the solvent is ordinarily 0.1 to 50 liters, preferably 0.2 to 3.0 liters relative to 1 mol of the compound [IV]. The use amount of the base is appropriately selected ordinarily in a range of to 10 equivalents relative to 1 equivalent of the compound [IV] and is preferably 1 to 5 equivalents.

The reaction temperature of the reaction is ordinarily any temperature from −20° C. to the reflux temperature of the reaction system and is preferably −10° C. to 100° C.

The reaction time of the reaction differs depending upon the reaction temperature, the substrate of reaction, the amount of reaction, etc., but is ordinarily 1 to 48 hours.

After the completion of the reaction, there are conducted operations such as poring of water into reaction mixture, extraction with organic solvent, concentration and the like, whereby the compound [VI] can be isolated. The isolated compound [VI] can be purified as necessary by column chromatography, recrystallization, etc.

(Step 2)

When $R^2=R^2$, the compound [VI] can be produced in one step without via the compound [IV] by reacting the compound [II] with a compound [III] in an appropriate solvent in the presence of an appropriate base.

The amount of the compound [III] used in the reaction is appropriately selected ordinarily in a range of 2 to 10 eluivalents relative to 1 equivalent of the compound [II] and is preferably 2 to 5 equivalents.

As the solvent and base usable in the reaction, there can be mentioned the same solvents and bases as mentioned in the (step 1-1). The use amount of the solvent is ordinarily 0.1 to 50 liters, preferably 0.2 to 3.0 liters relative to 1 mol of the compound [II]. The use amount of the base is appropriately selected ordinarily in a range of to 20 equivalents relative to 1 equivalent of the compound [II] and is preferably 2 to 10 equivalents.

The reaction temperature of the reaction is ordinarily any temperature from −20° C. to the reflux temperature of the reaction system and is preferably −10° C. to 100° C.

The reaction time of the reaction differs depending upon the reaction temperature, the substrate of reaction, the amount of reaction, etc., but is ordinarily 1 to 48 hours.

After the completion of the reaction, there are conducted operations such as poring of water into reaction mixture, extraction with organic solvent, concentration and the like, whereby the compound [VI] can be isolated. The isolated compound [VI] can be purified as necessary by column chromatography, recrystallization, etc.

[Production Method 2]

Of the glyoxime derivatives represented by the general formula, the compound represented by the general formula [VIII] can be produced, for example, by the following method.

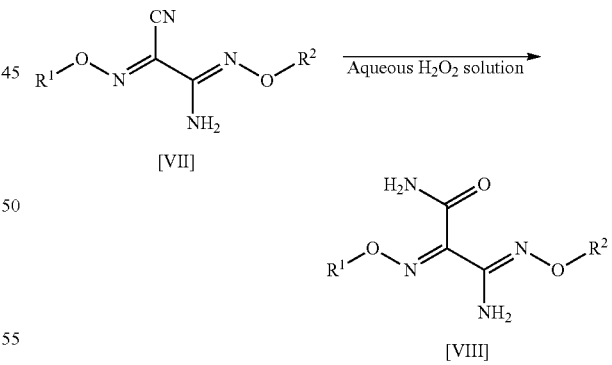

[Formula 4]

(In the formula, $R^1$ and $R^2$ have the same meanings as given above.)

The compound [VIII] can be produced by reacting a compound [VII] with an aqueous hydrogen peroxide solution in the presence of an appropriate base. An appropriate catalyst may be added in the production.

The use amount of the aqueous hydrogen peroxide solution is appropriately selected in a range of 1.0 to 20.0 mols relative to 1 mol of the compound [VII] and is preferably 1.0 to 6.0 mols.

In the reaction, a solvent may be used as necessary. As the solvent usable, there can be mentioned, for example, alcohols such as methanol, ethanol propanol and the like; halogenated hydrocarbons such as chloroform, dichloromethane and the like; sulfur compounds such as dimethyl sulfoxide, sulfolane and the like; water; and mixtures thereof. The amount of the solvent is ordinarily 0.1 to 50 liters, preferably 0.2 to 3 liters relative to 1 mol of the compound [VII].

As the base usable in the reaction, there can be mentioned, for example, inorganic bases such as alkali metal hydroxides (e.g. sodium hydroxide and potassium hydroxyide), alkali metal carbonates (e.g. sodium carbonate and potassium carbonate), alkali metal bicarbonates (e.g. sodium hydrogencarbonate and potassium hydrogencarbonate) and the like. The use amount of the base is appropriately selected ordinarily in a range of 0.1 to 10 equivalents relative to 1 equivalent of the compound [VII] and is preferably 0.1 to 2 equivalents.

As the catalyst usable in the reaction, there can be mentioned, for example, quaternary ammonium salts such as tetra-n-butylammonium hydrogensulfate, tetra-nbutylammonium bromide, tetra-n-butylammonium chloride and the like. The use amount of the catalyst is appropriately selected ordinarily in a range of 0.01 to 0.5 equivalent relative to 1 equivalent of the compound [VII] and is preferably 0.01 to 0.1 equivalent.

The reaction temperature of the reaction is ordinarily any temperature from −50° C. to the reflux temperature of the reaction system and is preferably 0° C. to 100° C.

The reaction time of the reaction differs depending upon the reaction temperature, the substrate of reaction, the amount of reaction, etc., but is ordinarily 1 to 48 hours.

After the completion of the reaction, there are conducted operations such as poring of water into reaction mixture, extraction with organic solvent, concentration and the like, whereby the compound [VIII] can be isolated. The isolated compound [VIII] can be purified as necessary by column chromatography, recrystallization, etc.

The pest control agent of the present invention is characterized by containing, as an active ingredient, a glyoxime derivative represented by the general formula [I] or an agriculturally acceptable salt thereof. The present pest control agent is representatively an insecticide.

Of the glyoxime derivatives represented by the general formula [I], the glyoxime derivatives represented by the general formula [I'] are novel compounds; and they and, as necessary, salts thereof are preferably used for pest control, particularly as insecticide.

The present pest control agent may as necessary contain an additive component (carrier) ordinarily used in agricultural chemical formulations.

As the additive component, there can be mentioned a carrier (e.g. solid carrier or liquid carrier), a surfactant, a binder or a tackifier, a thickening agent, a coloring agent, a spreader, a sticker, an anti-freeze, a solidification inhibitor, a disintegrator, a decomposition inhibitor, etc. As necessary, there may be used other additive components such as antiseptic, vegetable chip and the like.

These additive components may be used in one kind or in combination of two or more kinds. The above additive components are explained below.

As the solid carrier, there can be mentioned, for example, mineral carriers such as pyrophyllite clay, kaolin clay, silicastone clay, talc, diatomaceous earth, zeolite, bentonite, acid clay, active clay, Attapulgus clay, vermiculite, perlite, pumice, white carbon (e.g. synthetic silicic acid or synthetic silicate), titanium dioxide and the like; vegetable carriers such as wood flour, corn culm, walnut shell, fruit stone, rice hull, sawdust, wheat bran, soybean flour, powder cellulose, starch, dextrin, saccharide and the like; inorganic salt carriers such as calcium carbonate, ammonium sulfate, sodium sulfate, potassium chloride and the like; and polymer carriers such as polyethylene, polypropylene, polyvinyl chloride, polyvinyl acetate, ethylene-vinyl acetate copolymer, urea-aldehyde resin and the like.

As the liquid carrier, there can be mentioned, for example, monohydric alcohols such as methanol, ethanol, propanol, isopropanol, butanol, cyclohexanol and the like; polyhydric alcohols such as ethylene glycol, diethylene glycol, propylene glycol, hexylene glycol, polyethylene glycol, polypropylene glycol, glycerine and the like; polyhydric alcohol derivatives such as propylene-type glycol ether and the like; ketones such as acetone, methyl ethyl ketone, methyl isobutyl ketone, disobutyl ketone, cyclohexanone, isophorone and the like; ethers such as ethyl ether, dioxane, cellosolve, dipropyl ether, tetrahydrofuran and the like; aliphatic hydrocarbons such as normal paraffin, naphthene, isoparaffin, kerosene, mineral oil and the like; aromatic hydrocarbons such as toluene, $C_9$~$C_{10}$ alkylbenzene, xylene, solvent naphtha, alkylnaphthalene, high-boiling aromatic hydrocarbon and the like; halogenated hydrocarbons such as dichloroethane, chloroform, carbon tetrachloride and the like; esters such as ethyl acetate, diisopropyl phthalate, dibutyl phthalate, dioctyl phthalate, dimethyl adipate and the like; lactones such as γ-butyrolactone and the like; amides such as dimethylformamide, diethylformamide, dimethylacetamide, N-alkylpyrrolidinone and the like; nitriles such as acetonitrile and the like; sulfur compounds such as dimethyl sulfoxide and the like; vegetable oils such as soybean oil, rapeseed oil, cottonseed oil, coconut oil, castor oil and the like; and water.

As to the surfactant, there is no particular restriction. However, the surfactant preferably gels or swells in water. There can be mentioned, for example, non-ionic surfactants such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkylphenyl ether, polyoxyethylene dialkylphenyl ether, polyoxyethylene alkylphenyl ether-formalin condensate, polyoxyethylene polyoxypropylene block polymer, alkyl polyoxyethylene polypropylene block polymer ether, polyoxyethylene alkyl amine, polyoxyethylene fatty acid amide, polyoxyethylene fatty acid bisphenyl ether, polyalkylene benzyl phenyl ether, polyoxyalkylene styryl phenyl ether, acetylene diol, polyoxyalkylene-added acetylene diol, polyoxyethylene ether type silicone, ester type silicone, fluorine-containing surfactant, polyoxyethylene castor oil, polyoxyethylene hardened castor oil and the like; anionic surfactants such as alkyl sulfate, polyoxyethylene alkyl ether sulfate, polyoxyethylene alkyl phenyl ether sulfate, polyoxyethylene styryl phenyl ether sulfate, alkylbenzenesulfonic acid salt, ligninsulfonic acid salt, alkylsulfosuccinic acid salt, naphthalenesulfonic acid salt, alkylnaphthalenesulfonic acid salt, naphthalenesulfonic acid-formalin condensate salt, alkylnaphthalenesulfonic acid-formalin condensate salt, fatty acid salt, polycarboxylic acid salt, N-methyl-fatty acid sarcosinate, resin acid salt, polyoxyethylene alkyl ether phosphate, polyoxyethylene alkylphenyl ether phosphate and the like; cationic surfactants including alkyl amine salts such as laurylamine hydrochloride, stearylamine hydrochloride, oleylamine hydrochloride, stearylamine acetate, stearylaminopropylamine acetate, alkyl trimethyl ammonium chloride, alkyl dimethyl benzalkonium chloride and the like; and ampholytic surfactants such as betaine type (e.g. dialkyldiaminoethylbetaine or alkyldimethylbenzylbetaine), amino acid type (e.g. dialkylaminoethylglycine or alkyldimethylbenzylglycine) and the like.

As the binder and tackifier, there can be mentioned, for example, carboxymethyl cellulose or a salt thereof, dextrin, water-soluble starch, xanthane gum, guar gum, sucrose, polyvinylpyrrolidone, gum arabi, polyvinyl alcohol, polyvinyl acetate, sodium polyacrylate, polyethylene glycol having an average molecular weight of 6,000 to 20,000, polyethylene oxide having an average molecular weight of 100,000 to 5,000,000, and natural phospholipid (e.g. cephalinic acid or lecithin).

As the thickening agent, there can be mentioned, for example, water-soluble polymers such as xanthan gum, guar gum, carboxymethyl cellulose, polyvinylpyrrolidone, carboxyvinyl polymer, acrylic polymer, starch derivative, polysaccharide and the like; and inorganic fine powders such as high-purity bentonite, white carbon and the like.

As the coloring agent, there can be mentioned, for example, inorganic pigments such as iron oxide, titanium oxide, Prussian Blue and the like; and organic dyes such as Alizarine dye, azo dye, metal phthalocyanine dye and the like.

As the spreader, there can be mentioned, for example, silicone-based surfactant, cellulose powder, dextrin, processed starch, polyaminocarboxylic acid chelate compound, crosslinked polyvinylpyrrolidone, maleic acid and styrene, methacrylic acid copolymer, half ester between polyhydric alcohol polymer and dicarboxylic acid anhydride, and water-soluble salt of polystyrenesulfonic acid.

As the sticker, there can be mentioned, for example, surfactant (e.g. sodium dialkylsulfosuccinate, polyoxyethylene alkyl ether, polyoxyethylene alkylphenyl ether, or polyoxyethylene fatty acid ester), paraffin, terpene, polyamide resin, polyacrylic acid salt, polyoxyethylene, wax, polyvinyl alkyl ether, alkylphenol-formalin condensate, and synthetic resin emulsion.

As the anti-freeze, there can be mentioned, for example, polyhydric alcohol (e.g. ethylene glycol, diethyllene glycol, propylene glycol, or glycerine).

As the solidification inhibitor, there can be mentioned, for example, polysaccharide (e.g. starch, alginic acid, mannonse or galactose), polyvinylpyrrolidone, white carbon, ester gum and petroleum resin.

As the disintegrator, there can be mentioned, for example, sodium tripolyphosphate, sodium hexametaphosphate, stearic acid metal salt, cellulose powder, dextrin, methacrylic acid ester copolymer, polyvinylpyrrolidone, polyaminocarboxylic acid chelate compound, sulfonated styrene-isobutylene-maleic anhydride copolymer, and starchpolyacrylonitrile graft copolymer.

As the decomposition inhibitor, there can be mentioned, for example, desiccants such as zeolite, quick lime, magnesium oxide and the like; antioxidants such as phenol type, amine type, sulfur type, phosphoric acid type and the like; and ultraviolet absorbents such as salicylic acid type, benzophenone type and the like.

When the present pest control agent contains the above-mentioned additive components, their contents based on mass are selected in a range of ordinarily 5 to 95%, preferably 20 to 90% in the case of carrier, ordinarily 0.1 to 30%, preferably 0.5 to 10% in the case of surfactant, and ordinarily 0.1 to 30%, preferably 0.5 to 10% in the case of other additives.

The present pest control agent is used in any formulation selected from dust formulation, dust-granule mixture, granule, wettable powder, water-soluble concentrate, water dispersible granule, tablet, Jumbo, emulsifiable concentrate, oil formulation, solution, flowable concentrate, emulsion, microemulsion, suspoemulsion, ultra-low volume formulation, microcapsule, smoking agent, aerosol, baiting agent, paste, etc.

In actual use of the formulation, the formulation can be used per se or after dilution with a diluent (e.g. water) in a given concentration. The application of the formulations containing the present compound or of its dilution product can be conducted by a method ordinarily used, such as dispersion (e.g. spraying, misting, atomizing, powder dispersion, granule dispersion, on-water-surface dispersion, or in-box dispersion), in-soil application (e.g. mixing or drenching), on-surface application (e.g. coating, dust coating or covering), immersion, poison bait, smoking and the like. It is also possible to mix the above-mentioned active ingredient with a livestock feed in order to prevent the infestation and growth of injurious pest, particularly injurious insect in the excreta of livestock.

The proportion of the active ingredient in the present pest control agent is appropriately selected so as to meet the necessity. The active ingredient is appropriately selected, for example, in the following range. In dust formulation, dust-granule mixture, etc.

0.01 to 20% (mass), preferably 0.05 to 10% (mass) In granule, etc.

0.1 to 30% (mass), preferably 0.5 to 20% (mass) In wettable powder, water dispersible granule, etc.

1 to 70% (mass), preferably 5 to 50% (mass) In water-soluble concentrate, solution, etc 1-95% (mass), preferably 10 to 80% (mass) In emulsifiable concentrate, etc.

5 to 90% (mass), preferably 10 to 80% (mass) In oil formulation, etc.

1 to 50% (mass), preferably 5 to 30% (mass) In flowable concentrate, etc.

5 to 60% (mass), preferably 10 to 50% (mass) In emulsion, microemulsion, suspoemulsion, etc.

5 to 70% (mass), preferably 10 to 60% (mass) In tablet, baiting agent, paste, etc.

1 to 80% (mass), preferably 5 to 50% (mass) In smoking agent, etc.

0.1 to 50% (mass), preferably 1 to 30% (mass) In aerosol, etc.

0.05 to 20% (mass), preferably 0.1 to 10% (mass)

The formulation is sprayed after dilution in an appropriate concentration, or applied directly.

When the present pest control agent is used after dilution with a diluent, the concentration of active ingredient is generally 0.1 to 5,000 ppm. When the formulation is used per se, the application amount thereof per unit area is 0.1 to 5,000 g per 1 ha in terms of active ingredient compound; however, the application amount is not restricted thereto.

Incidentally, the present pest control agent is sufficiently effective when using the present compound alone as an active ingredient. However, in the present pest control agent, there may be mixed or used in combination, as necessary, fertilizers and agricultural chemicals such as insecticide, acaricide, nematicide, synergist, fungicide, anti-viral agent, attractant, herbicide, plant growth-controlling agent and the like. In this case, a higher effect is exhibited.

Below are shown examples of the known insecticide compounds, acaricide compounds, nematicide compounds and synergist compounds, which may be mixed or used in combination. However, other such compounds may be mixed or used in combination.

1. Acetylcholinesterase Inhibitors (1A) Carbamates: alanycarb, aldicarb, aldoxycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, xylylcarb;

(1B) Organophosphates: acephate, azamethiphos, azinphosethyl, azinphos-methyl, cadusafos, chlorethoxyfos, chlorfenvinphos, chlormephos, chlorpyrifos, chlorpyrifosmethyl, coumaphos, cyanophos, demoton-5-methyl, diamidafos, diazinon, dichlorvos, dicrotophos, dimethoate, dimethylvinphos, dioxabenzofos, disulfoton, DSP, EPN, ethion, ethoprophos, etrimfos, famphur, fenamiphos, fenitrothion, fenthion, fonofos, fosthiazate, fosthietan, heptenophos, isamidofos, isazophos, isofenphos-methyl, isopropyl O-(methoxyaminothio-phosphoryl)salicylate, isoxathion, malathion, mecarbam, methamidophos, methidathion, mevinphos, monocrotophos, naled, omethoate, oxydemeton-methyl, oxydeprofos, parathion, parathion-methyl, phenthoate, phorate, phosalone, phosmet, phosphamidon, phoxim, pirimiphos-methyl, profenofos, propaphos, propetamphos, prothiofos, pyraclofos, pyridaphenthion, quinalphos, sulfotep, tebupirimfos, temephos, terbufos, tetrachlorvinphos, thiometon, thionazin, triazophos, trichlorfon, vamidothion, dichlofenthion, imicyafos, isocarbophos, mesulfenfos, fluprazofos 2. GABA-Gated Chloride Channel Antagonists
(2A) Cyclodiene organochlorines: chlordane, endosulfan, gamma-BCH;
(2B) Phenylpyrazoles: acetoprol, ethiprole, fipronil, pyrafluprole, pyriprole, RZI-02-003 (code number), flufiprole 3. Sodium Channel Modulators
(3A) Pyrethroids/Pyrethrins: acrinathrin, allethrin (includes d-cis-trans and d-trans), bifenthrin, bioallethrin, bioallethrin S-cyclopentenyl, bioresmethrin, cycloprothrin, cyfluthrin (includes beta-), cyhalothrin (includes gamma- and lambda-), cypermethrin (includes alpha-, beta-, theta- and zeta-), cyphenothrin [includes (IR)-trans-isomers], deltamethrin, empenthrin, esfenvalerate, etofenprox, fenpropathrin, fenvalerate, flucythrinate, flumethrin, taufluvalinate (includes tau-), halfenprox, imiprothrin, metofluthrin, permethrin, phenothrin [includes (IR)-transisomer], prallethrin, profluthrin, pyrethrine, resmethrin, RU15525 (code number), silafluofen, tefluthrin, tetramethrin, tralomethrin, transfluthrin, ZX18901 (code number), fluvalinate, tetramethylfluthrin, meperfluthrin, heptafluthrin;
(3B) DDT/Methoxychlor: DDT, methoxychlor 4. Nicotinic Acetylcholine Receptor Agonist/Antagonist
(4A) Neonicotinoids: acetamiprid, clothianidin, dinotefuran, imidacloprid, nitenpyram, thiacloprid, thiamethoxam;
(4B) Nicotine: nicotine-sulfate 5. Nicotinic Acetylcholine Receptor Allosteric Activators
Spinosyns: Spinetoram, Spinosad 6. Chloride Channel Activators
Avermectins, Milbemycins: abamectin, emamectin benzoate, lepimectin, milbemectin, ivermectin, polynactins 7. Juvenile Hormone Mimics
diofenolan, hydroprene, kinoprene, methothrin, fenoxycarb, pyriproxyfen 8. Miscellaneous Non-Specific (Multi-Site) Inhibitors
1,3-dichloropropene, DCIP, ethylene dibromide, methyl bromide, chloropicrin, sulfuryl fluoride 9. Antifeedant
pymetrozine, flonicamid 10. Mite Growth Inhibitors
clofentezine, diflovidazin, hexythiazox, etoxazole 11. Microbial Disruptors of Insect Midgut Membranes
BT agents: *Bacillus sphaericus, Bacillus thuringiensis* subsp. *aizawai, Bacillus thuringiensis* subsp. *israelensis, Bacillus thuringiensis* subsp. *kurstaki, Bacillus* thuringiensis subsp. *tenebrionis*, Bt crop proteins (Cry1Ab, Cry1Ac, Cry1Fa, Cry2Ab, mCry3A, Cry3Ab, Cry3Bb, Cry34/35Ab1), *Bacillus popilliae, Bacillus* subtillis 12. Inhibitors of Mitochondrial ATP Synthase
diafenthiuron;
Organotin miticides: azocyclotin, cyhexatin, fenbutatin oxide;
propargite, tetradifon 13. Uncouplers of Oxidative Phosphorylation Via Disruption of the Proton Gradient
chlorfenapyr, DNOC 14. Nicotinic Acetylcholine Receptor Channel Blockers
Nereistoxin analogues: bensultap, cartap, thiocyclam, thiosultap 15. Inhibitors of Chitin Biosynthesis, Type 0
Benzoylureas: bistrifluoron, chlorfluazuron, diflubenzuron, flucycloxuron, flufenoxuron, hexaflumuron, lufenuron, novaluron, noviflumuron, teflubenzuron, triflumuron, fluazuron 16. Inhibitors of Chitin Biosynthesis, Type 1 Buprofezin 17. Moulting Disruptor, Dipteran
cyromazine 18. Ecdysone Receptor Agonist (Ecdysis Acceleration)
Diacylhydrazines: chromafenozide, halofenozide, methoxyfenozide, tebufenozide 19. Octopamine Receptor Agonist
amitraz 20. Mitochondrial Complex III Electron Transport Inhibitors
hydramethylnon, acequinocyl, fluacrypyrim, pyriminostrobin 21. Mitochondrial Complex II Electron Transport Inhibitors
cyflumetofen, cyenoprafen, pyflubumide 22. Mitochondrial Complex I Electron Transport Inhibitors
METI acaricides and insecticides: fenazaquin, fenpyroximate, pyridaben, pyrimidifen, tebufenpyrad, tolfenpyrad
Other: rotenone 23. Sodium Channel Blockers
indoxacarb, metaflumizone 24. Inhibitors of Lipid Synthesis
Tetronic and Tetramic acid derivatives: spirodiclofen, spiromesifen, spirotetramat 25. Mitochondrial Complex IV Electron Transport Inhibitors
aluminium phosphide, phosphine, zinc phosphide, calcium cyanide 26. Neuronal Inhibitors (Unknown Mode of Action)
bifenazate 27. Aconitase Inhibitors
sodium fluoroacetate 28. Synergists
piperonyl butoxide, DEF 29. Ryanodine Receptor Modulators
chlorantraniliprole, flubendiamide, cyantraniliprole 30. Compounds with Unknown Mode of Action
azadirachtin, amidoflumet, benclothiaz, benzoximate, bromopropylate, chinomethionat, CL900167 (code number), cryolite, dicofol, dicyclanil, dienochlor, dinobuton, fenbutatin oxide, fenothiocarb, fluensulfone, flufenerim, fulsulfamide, karanjin, metham, methoprene, methoxyfenozide, methyl isothiocyanate, pyridalyl, pyrifluquinazon, sulcofuron-sodium, sulfluramid, sulfoxaflor, flupyradifurone, flometoquin, IKI-3106 (code number), afidopyropen, rescalure, NA-85 (code number)

31. Entomopathogenic Fungi, Nematode-Pathogenic Microorganisms
*Beauveria bassiana, Beauveria tenella, Verticillium lecanii, Pacilimyces tenuipes, Paecilomyces fumosoroceus, Beauveria* brongniartii, Monacrosporium phymatophagum, Pasteuriapenetrans 32. Sex Pheromone (Z)-11-hexadecenal, (Z)-11-hexadecenyl acetate, litlure-A, litlure-B, Z-13-eicosene-10-one, (Z,E)-9,12-tetradecadienyl acetate, (Z)-9-tetradecen-1-ol, (Z)-11-tetradecenyl acetate, (Z)-9,12-tetradecadienyl acetate, (Z,E)-9,11-detradecadienyl acetate Below are shown examples of the known fungicide or disease damage control agent compounds which may be mixed or used in combination. However, other such compounds may be mixed or used in combination.

1. Nucleic Acid Biosynthesis Inhibitors

Acylalanines: benalazyl, benalazyl-M, furalaxyl, metalaxyl, metalaxyl-M;
Oxazolidinones: oxadixyl;
Butyrolactones: clozylacon, ofurace;
Hydroxy-(2-amino)pyrimidines: bupirimate, dimethirimol, ethirimol;
Isoxazoles: hymexazol;
Isothiazolones: octhilinone;
Carboxylic acids: oxolinic acid 2. Mitosis and Cell Division Inhibitors Benzoimidazoles: benomyl, carbendazim, fuberidazole, thiabendazole;
Thiophanates: thiophanate, thiophanate-methyl;
N-phenylcarbamates: diethofencarb;
Toluamides: zoxamide;
Phenylureas: pencycuron;
Pyridinylmethylbenzamides: fluopicolide 3. Respiratory Inhibitors Pyrimidinamines: diflumetorim;
Carboxamides: benodanil, flutolanil, mepronil, fluopyram, fenfuram, carboxin, oxycarboxin, thifluzamide, bixafen, furametpyr, isopyrazam, penflufen, penthiopyrad, sedaxane, boscalid, fluxapyroxad, isofetamid, benzovindiflupyr;
Methoxy-acrylates: azoxystrobin, enestroburin, picoxystrobin, pyraoxystrobin, coumoxystrobin, enxastrobin, flufenoxystrobin;
Methoxy-carbamates: pyraclostrobin, pyrametostrobin, triclopyricarb;
Oxyimino acetates: kresoxim-methyl, trifloxystrobin;
Oxyimino-acetamides: dimoxystrobin, metominostrobin, orysastrobin, fenaminstrobin;
Oxazolidine-diones: famoxadone;
Dihydro-dioxazines: fluoxastrobin;
Imidazolinones: fenamidone;
Benzyl-carbamates: pyribencarb;
Cyano-imidazoles: cyazofamid;
Sulfamoyl-triazoles: amisulbrom;
Dinitrophenyl crotonates: binapacryl, methyldinocap, dinocap;
2,6-Dinitro-anilines: fluazinam;
Pyrimidinone hydrazones: ferimzone;
Tri phenyl tin compounds: TPTA, TPTC, TPTH;
Thiophene-carboxamides: silthiofam;
Triazolo-pyrimidylamines: ametoctradin 4. Amino Acid and Protein Synthesis Inhibitors Anilino-pyrimidines: cyprodinil, mepanipyrim, pyrimethanil;
Enopyranuronic acid antibiotic: blasticidin-S, mildiomycin;
Hexopyranosyl antibiotic: kasugamycin;
Glucopyranosyl antibiotic: streptomycin;
Tetracycline antibiotic: oxytetracycline 5. Signal Transduction Inhibitors Aryloxyquinoline: quinoxyfen;
Quinazolines: proquinazid;
Phenylpyrroles: fenpiclonil, fludioxonil;
Dicarboxylmides: chlozolinate, iprodione, procymidone, vinclozolin 6. Lipid Synthesis and Membrane Integrity Inhibitors Phosphoro-thiolates: edifenphos, iprobenfos, pyrazophos;
Dithiolanes: isoprothiolane;
Aromatic hydrocarbons: biphenyl, chloroneb, dicloran, quintozenes, tecnazene, tolclofos-methyl;
1,2,4-Thiadiazoles: etridiazole
Carbamates: iodocarb, propamocarb-hydrochloride, prothiocarb;
Cinnamic acid amides: dimethomorph, flumorph;
Valineamide carbamates: benthiavalicarb-isopropyl, iprovalicarb, valifenalate;
Mandelic acid amides: mandipropamid;
*Bacillus subtilis* and the fungicidal lipopeptides produced: *Bacillus subtilis* (strain: QST 713)

7. Inhibitors of Sterol Biosynthesis in Membranes piperazines: triforine;
Pyridines: pyrifenox;
Pyrimidines: fenarimol, nuarimol;
Imidazoles: imazalil, oxpoconazole-fumarate, pefurazoate, prochloraz, triflumizole;
Triazoles: azaconazole, bitertanol, bromuconazole, cyproconazole, difenoconazole, diniconazole, diniconazole-M, epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole, furconazole, furconazole-cis, quinconazole;
Morpholines: aldimorph, dodemorph, fenpropimorph, tridemorph;
Piperidines: fenpropidin, piperalin;
Spiroketal amines: spiroxamine;
Hydroxyanilides: fenhexamid;
Thiocarbamates: pyributicarb;
Allylamines: naftifine, terbinafine 8. Glucan Synthesis Inhibitors Glucopyranosyl type antibiotic: validamycin;
Peptidylpyridine nucleotide compound: polyoxin 9. Melanine Synthesis Inhibitors Isobenzo-furanones: phthalide;
Pyrrolo-quinolines: pyroquilon;
Triazolobenzo-thiazoles: tricyclazole;
Carboxamides: carpropamid, diclocymet;
Propionamides: fenoxanil 10. Host Plant Defence Inducers Benzo-thiadiazoles: acibenzolar-5-methyl;
Benzoisothiazoles: probenazole;
Thiadiazole-carboxamides: tiadinil, isotianil
Natural compound: laminarin 11. Compounds with Unknown Mode of Action Copper compound: copper hydroxide, copper dioctanoate, copper oxychloride, copper sulfate, cuprous oxide, oxine-copper, Bordeaux mixture, copper nonyl phenol sulphonate;
Sulfur compound: sulfur;
Dithiocarbamates: ferbam, mancozeb, maneb, metiram, propineb, thiram, zineb, ziram, cufraneb;
Phthalimides: captan, folpet, captafol;
Chloronitriles: chlorothalonil;
Sulfamides: dichlofluanid, tolylfluanid;
Guanidines: guazatine, iminoctadine-albesilate, iminoctadine-triacetate, dodine;
Other compound: anilazine, dithianon, cymoxanil, fosetyl (alminium, calcium, sodium), phosphorus acid and salts, tecloftalam, triazoxide, flusulfamide, diclomezine, methasulfocarb, ethaboxam, cyflufenamid, metrafenone, potassium bicarbonate, sodium bicarbonate, BAF-045 (code number), BAG-010 (code number), benthiazole, bronopol, carvone, chinomethionat, dazomet, DBEDC, debacarb, dichlorophen, difenzoquat-methyl sulfate, dimethyl disulfide, diphenylamine, ethoxyquin, flumetover, fluoroimide, flutianil, furancarboxylic acid, metam, nabam, natamycin, nitrapyrin, nitrothal-isopropyl, o-phenylphenol, oxazinylazole, oxyquinoline sulfate, phenazine oxide, polycarbamate, pyriofenone, fenpyrazamine, silver, pyrisoxazole, tebufloquin, tolnifanide, trichlamide, mineral oils, organic oils, tolprocarb, oxathiapiprolin Below are shown examples of the known herbicidal compounds and plant growth-controlling compounds which may be mixed or used in combination. However, the compounds are not restricted to these examples.

A1. Acetyl CoA Carboxylase (ACCase) Inhibitors
(A1-1) Aryloxyphenoxy propionate: clodinafop-propargyl, cyhalofop-butyl, diclofop-methyl, diclofop-P-methyl, fenoxaprop-P-ethyl, fluazifop-butyl, fluazifop-P-butyl, haloxyfop, haloxyfop-etotyl, haloxyfop-P, metamifop, propaquizafop, quizalofop-ethyl, quizalofop-P-ethyl, quizalofop-P-tefuryl, fenthiaprop-ethyl;
(A1-2) Cyclohexandiones: alloxydim, butroxydim, clethodim, cycloxydim, profoxydim, sethoxydim, tepraloxydim, tralkoxydim;
(A1-3) Phenylpyrazolines: Aminopyralid, Pinoxaden;

B. Acetolactic Synthase (ALS) Inhibitors
(B-1) Imidazolinones: imazamethabenz-methyl, imazamox, imazapic (includes salts with amine, etc.), imazapyr (includes salts with isopropylamine, etc.), imazaquin, imazathapyr;
(B-2) Pyrimidinyloxy benzoate: bispyribac-sodium, pyribenzoxim, pyriftalid, pyriminobac-methyl, pyrithiobac-sodium, pyrimisulfan, triafamone;
(B-3) Sulfonylaminocarbonyl-triazolinones: flucarbazonesodium, thiencarbazone (includes sodium salt, methyl ester, etc.), propoxycarbazone-sodium, procarbazone-sodium, iofensulfuran-sodium;
(B-4) Sulfonylureas: amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, foramsulfuron, halosulfuron-methyl, imazosulfuron, iodosulfulon-methyl-sodium, mesosulfuron-methyl, thifensulfuronmethyl, triasulfuron, tribenuron-methyl, trifloxysulfuronsodium, triflusulfuron-methyl, tritosulfuron, orthosulfamuron, propyrisulfuron, metazosulfuron, flucetosulfuron;
(B-5) Triazolopyrimidines: cloransulam-methyl, diclosulam, florasulam, flumetsulam, metosulam, penoxsulam, pyroxsulam;

C1. Photosynthesis at Photosystem II Inhibitors (1)
(C1-1) Phenyl-carbamates: desmedipham, phenmedipham;
(C1-2) Pyridazinones: chloridazon, brompyrazon;
(C1-3) Triazines: ametryn, atrazine, cyanazine, desmetryne, dimethametryn, eglinazine-ethyl, prometon, prometryn, propazine, simazine, simetryn, terbumeton, terbuthylazine, terbutryn, trietazine;
(C1-4) Triazinones: metamitron, metribuzin;
(C1-5) Triazolinones: amicarbazone;
(C1-6) Uracils: bromacil, lenacil, terbacil;

C2. Photosynthesis at Photosystem II Inhibitors (2)
(C2-1) Amides: pentanochlor, propanil;
(C2-2) Ureas: chlorbromuron, chlorotoluron, chloroxuron, dimefuron, diuron, ethidimuron, fenuron, fluometuron, isoproturon, isouron, linuron, methabenzthiazuron, metobromuron, metoxuron, monolinuron, neburon, siduron, tebuthiuron, metobenzuron;

C3. Photosynthesis at Photosystem II Inhibitors (3)
(C3-1) Benzothiadiazones: bentazone;
(C3-2) Nitriles: bromofenoxim, bromoxynil (includes esters of butyric acid, octanoic acid, heptanoic acid, etc.), ioxynil;
(C3-3) Phenylpyrazines: pyridafol, pyridate;

D. Photosystem-1-Electron Acceptors
(D-1) Bipyridyliums: diquat, paraquat dichloride;

E. Protoporphyrinogen oxidase (PPO) inhibitors
(E-1) Diphenylethers: acifluorfen-sodium, bifenox, chlomethoxyfen, ethoxyfen-ethyl, fluoroglycofen-ethyl, fomesafen, lactofen, oxyfluorfen;
(E-2) N-phenylphthalimides: cinidon-ethyl, flumiclorac-pentyl, flumioxazin, chlorphthalim;
(E-3) Oxydiazoles: oxadiargyl, oxadiazon;
(E-4) Oxazolidinediones: pentoxazone;
(E-5) Phenylpyrazoles: fluazolate, pyraflufen-ethyl;
(E-6) Pyrimidinediones: benzfendizone, butafenacil, saflufenacil;
(E-7) Thiadiazoles: fluthiacet-methyl, thidiazimin;
(E-8) Triazolinones: azafenidin, carfentrazone-ethyl, sulfentrazone, bencarbazone;
(E-9) Other compound: flufenpyr-ethyl, profluazol, pyraclonil, SYP-298 (code number), SYP-300 (code number);

F1. Inhibitors of Carotenoid Biosynthesis at the Phytoene Desaturase Step (PDS)
(F1-1) Pyridazinones: norflurazon;
(F1-2) Pyrimidinecarboxamides: diflufenican, picolinafen;
(F1-3) Other compound: beflubutamid, fluridone, fluorochloridone, flurtamone;

F2. 4-Hydroxyphenylpyruvate dioxygenase (HPPD) inhibitors
(F2-1) Callistemones: mesotrione;
(F2-2) Isoxazoles: pyrasulfotole, isoxaflutole, isoxachlortole;
(F2-3) Pyrazoles: benzfenap, pyrazolynate, pyrazoxyfen, topramezone;
(F2-4) Ttiketones: sulcotrione, tefuryltrion, tembotrione, pyrasulfotole, bicyclopyrone;

F3. Carotinoid Biosynthesis Inhibitors (Unknown Target)
(F3-1) Diphenylethers: aclonifen;
(F3-2) Isoxazolidinones: clomazone;
(F3-3) Triazoles: amitrole;

G. EPSP Synthase Inhibitors (Aromatic Amino Acid Biosynthesis Inhibitors)
(G-1) Glycines: glyphosate (includes salts of sodium, amine, propylamine, ispropylamine, dimethylamine, trimesium etc.);

H. Glutamine Synthetase Inhibitors
(H-1) Phosphinic acids: bilanafos, glufosinate (includes salts of amine, sodium, etc.);

I. Dihydropteroate (DHP) Inhibitors
(1-1) Carbamates: asulam;

K1. Microtubule Assembly Inhibitors
(K1-1) Benzamides: propyzamide, tebutam;
(K1-2) Benzoic acids: chlorthal-dimethyl;
(K1-3) Dinitroanilines: benfluralin, butralin, dinitramine, ethalfluralin, fluchloralin, oryzalin, pendimethalin, prodiamine, trifluralin;
(K1-4) Phosphoroamidates: amiprofos-methyl, butamifos;
(K1-5) Pyridines: dithiopyr, thiazopyr;

K2. Inhibitors of Mitosis/Microtubule Organization
  (K2-1) Carbamates: carbetamide, chlorpropham, propham, swep, karbutilate;
K3. Very-Long-Chain Fatty Acids (VLCFAs) Inhibitors (Cell Division Inhibitors)
  (K3-1) Acetamides: diphenamid, napropamide, naproanilide;
  (K3-2) Chloroacetamides: acetochlor, alachlor, butachlor, butenachlor, diethatyl-ethyl, dimethachlor, dimethenamid, dimethenamid-P, metazachlor, metolachlor, pethoxamid, pretilachlor, propachlor, propisochlor, S-metholachlor, thenylchlor;
  (K3-3) Oxyacetamides: flufenacet, mefenacet;
  (K3-4) Tetrazolinones: fentrazamide;
  (K3-5) Other compound: anilofos, bromobutide, cafenstrole, indanofan, piperophos, fenoxasulfone, pyroxasulfone, ipfencarbazone;
L. Cellulose Synthesis Inhibitors
  (L-1) Benzamides: isoxaben;
  (L-2) Nitriles: dichlobenil, chlorthiamid;
  (L-3) Triazolocarboxamides: flupoxame;
M. Uncouplers (Membrane Disruptors)
  (M-1) Dinitrophenols: dinoterb, DNOC (includes salts of amine, sodium, etc.);
N. Lipid Synthesis Inhibitors (Excluding ACCase Inhibitors)
  (N-1) Benzofurans: benfuresate, ethofumesate;
  (N-2) Halogenated carboxylic acids: dalapon, flupropanate, TCA (includes salts of sodium, calcium, ammonia, etc.);
  (N-3) Phosphorodithioates: bensulide;
  (N-4) Thiocarbamates: butylate, cycloate, dimepiperate, EPTC, esprocarb, molinate, orbencarb, pebulate, prosulfocarb, thiobencarb, tiocarbazil, tri-allate, vernolate
O. Synthetic Auxins
  (O-1) Benzoic acids: chloramben, 2,3,6-TBA, dicamba (includes salts of amine, diethylamine, isopropylamine, diglycolamine, sodium, lithium, etc.);
  (O-2) Phenoxycarboxylic acids: 2,4,5-T, 2,4-D (includes salts of amine, diethylamine, triethanolamine, isopropylamine, sodium, lithium, etc.), 2,4-DB, clomeprop, dichlorprop, dichlorprop-P, MCPA, MCPA-thioethyl, MCPB (includes sodium salt, ethylester, etc.), mecoprop (includes salts of sodium, potassium, isopropylamine, trietanolamine, dimethylamine, etc.), mecoprop-P;
  (O-3) Pyridine carboxylic acids: clopyralid, fluoroxypyr, picloram, triclopyr, triclopyr-butotyl;
  (O-4) Quinoline carbxylic acids: quinclorac, quinmerac;
  (O-5) Other compound: benazolin;
P. Auxin Transport Inhibitors
  (P-1) Phthalamates: naptalam (includes salts with sodium, etc.);
  (P-2) Semicarbazones: diflufenzopyr;
Z. Compounds with Unknown Mode of Action flamprop-M (includes methyl, ethyl and isopropyl esters), flamprop (includes methyl, ethyl and isopropyl esters), chlorflurenol-methyl, cinmethylin, cumyluron, daimuron, methyldymuron, difenzoquat, etobenzanid, fosamine, pyributicarb, oxaziclomefone, acrolein, AEF-150944 (code number), aminocyclopyrachlor, cyanamide, heptamaloxyloglucan, indaziflam, triaziflam, quinoclamine, endothaldisodium, phenisopham, SL-573 (code number), SW-065 (code number)
  Plant growth-controlling agent: 1-methylcyclopropene, 1-naphthylacetamide, 2,6-diisopropylnaphthalene, 4-CPA, benzylaminopurine, ancymidol, aviglycine, carvone, chlormequat, cloprop, cloxyfonac, cloxyfonac-potassium, cyclanilide, cytokinins, daminozide, dikegulac, dimethipin, ethephon, ethychlozate, flumetralin, flurenol, flurprimidol, forchlorfenuron, gibberellin acid, inabenfide, indole acetic acid, indole butyric acid, maleic hydrazide, mefluidide, mepiquat chloride, n-decanol, paclobutrazol, prohexadionecalcium, prohydrojasmon, sintofen, thidiazuron, triacontanol, trinexapac-ethyl, uniconazole, uniconazole-P, 4-oxo-4-(2-phenylethyl)aminobutyric acid (chemical name, CAS registration No.: 1083-55-2)

Below are shown examples of the known chemical injury-reducing compounds which may be mixed or used in combination. However, the compounds are not restricted to these examples.

benoxacor, furilazole, dichlormid, dicyclonone, DKA-24 (N1,N2-diallyl-N2-dichloroacetylglycineamide), AD-67 (4-dichloroacetyl-1-oxa-4-azaspiro[4.5]decane), PPG-1292 (2,2-dichloro-N-(1,3-dioxan-2-ylmethyl)-N-(2-propenyl)acetamide), R-29148 (3-dichloroacetyl-2,2,5-trimethyl-1,3-oxazoline), cloquintcet-mexyl, 1,8-Naphthalic Anhydride, mefenpyrdiethyl, mefenpyr, mefenpyr-ethyl, fenchlorazole-O-ethyl, fenclorim, MG-191 (2-dichloromethyl-2-methyl-1,3-dioxane), cyometrinil, flurazole, fluxofenim, isoxadifen, isoxadifenethyl, mecoprop, MCPA, daimuron, 2,4-D, MON 4660 (code number), oxabetrinil, cyprosulfamide, lower alkyl-substituted benzoic acid, TI-35 (code number), N-(2-methoxybenzolyl)-4-[(methylaminocarbonyl)amino]benzenesulfonamide (chemical name, CAS registration No.: 129531-12-0)

The pest control agent of the present invention shows an excellent control effect to pests of Orthoptera, Thysanoptera, Hemiptera, Coleoptera, Diptera, Lepidoptera, Hymenoptera, Collembola, Thysanura, Blattodea, Isoptera, Psocoptera, *Mallophaga, Anoplura*, plant-feeding mites, plant parasitic nematodes, plant parasitic mollusc pests, other crop pests, nuisance pests, sanitary insects, parasites, etc. As examples of such pests, the following organism species can be mentioned.

As the Orthopteran pest, there can be mentioned, for example,
  Tettigoniidae: Ruspolia lineosa, etc.,
  Gryllidae: Teleogryllus emma, etc.,
  Gryllotalpidae: *Gryllotalpa* orientalis,
  Locustidae: Oxya hyla intricate, *Locusta migratoria, Melanoplus sanguinipes*, etc.,
  Pyrgomorphidae: Atractomorpha lata,
  Acrididae: Euscyrtus japonicus
  Tridactylidae: Xya japonicus, etc.

As the Thysanopteran pests, there can be mentioned, for example,
  Thripidae: *Frankliniella intonsa, Frankliniella* occidentalis, *Scirtothrips dorsalis, Thrips palmi, Thrips tabaci*, etc.,
  Phlaeothripidaes: Ponticulothrips diospyrosi, Haplothrips aculeatus, etc.

As the Hemipteran pest, there can be mentioned, for example,
  Cicadidae: Mogannia minuta, etc.,
  Cercopidae: Aphorphora intermedia, etc.,
  Membracidae: Machaerotypus sibiricus, etc.,
  Deltcephalidae: *Arboridia apicalis, Empoasca onukii, Nephotettix cincticeps, Recilia dorsalis*, etc.,
  Cixiidae: Pentastiridius apicalis, etc., *Delphacidae: Laodelphax striatellus, Nilaparvata lugens, Sogatella furcifera*, etc.,
  Meenoplidae: Nisia nervosa, etc.,
  Derbidae: Kamendaka saccharivora, etc.,
  Cixidia okunii: Achilus flammeus, etc.,
  Ricamidae: Orosanga japonicus, etc.,
  Flatidae: Mimophantia maritima, etc.,
  Psyllidae: Cacopsylla pyrisuga, etc.,
  Calophyidae: Calophya mangiferae, etc.,
  Phylloxeridae: Daktulosphaira vitifoliae, etc., Chemidae: Adelges laricis,
Adelgidae: Adelges tsugae, etc.,
Aphididae: *Acyrthosiphon pisum, Aphis gossypii, Aphis spiraecola, Lipaphis erysimi, Myzuspersicae, Schizaphis graminum, Rhopalosiphum padi*, etc.,
Aleyrodidae: *Aleurocanthus spiniferus, Bemisia tabaci, Bemisia argentifolii, Trialeurodes vaporariorum*, etc.,
Margarodidae: *Drosicha corpulenta, Icerya purchasi*, etc.,
Pseudococcidae: *Dysmicoccus brevipes, Planococcus citri, Pseudococcus comstocki*, etc.,
Coccidae: Ceroplastes ceriferus, etc.,
Aclerdidae: Aclerda takahasii, etc.,
Diaspididae: Aonidella aurantii, Diaspidiotus perniciosus, *Unaspis yanonensis*, etc.,
Miridae: *Lygus hesperus, Trigonotylus caelestialium*, etc.,
Tingitidae: *Stephanitis pyrioides, Stephanitis nashi*, etc.,
Pentatomidae: *Eysarcoris* aeneus, Lagynotomus elongatus, *Nezara viridula, Plautia* crssota, etc.,
Plataspidae: Megacopta cribaria, etc.,
Lygaeidae: Cavelerius saccharivorus, etc.,
Malcidae: Malcus japonicus, etc.,
*Pyrrhocoridae: Dysdercus* cingulatus, etc.,
Alydidae: *Leptocorisa acuta, Leptocorisa* chinensis, etc.,
*Coreidae*: Anacanthocoris striicornis, etc.,
Rhopalidae: Rhopalus maculatus, etc.,
*Cimicidae*: Cimex lectularius, etc.
As the Coleoptera pests, there can be mentioned, for example,
Scarabaeidae: Anomara cuprea, Anomara rufocuprea, Popillia japonica, Oryctes rhinoceros, etc.,
Elateridae: *Agriotes ogurae, Melanotus okinawensis, Melanotos fortnumi*, etc.,
Dermestidae: Anthrenus verbasci, etc.,
Bostrichidae: Heterobostrychus hamatipennis, etc.,
Anobiidae: Stegobium paniceum, etc.,
Ptimidae: Pitinus clavipes, etc.,
Trogositidae: Tenebroides manritanicus, etc.,
Cleridae: Necrobia rufipes,
Nitidulidae: Carpophilus hemipterus, etc.,
Silvanidae: Ahasverus advena, etc.,
Laemophloeidae: cryptolestes ferrugineus, etc.,
Coccinellidae: *Epilachna varivestis, Henosepilachna vigintioctopunctata*, etc.,
Tenebrionidae: *Tenebrio molitor, tribolium castaneum*, etc.,
Meloidae: Epicauta gorhami, etc.,
Cerambycidae: *Anoplophora* glabripennis, Xylotrechus pyrroderus, Monochamus alternatus, etc.,
Bruchidae: *Callosobruchus chinensis*, etc.,
*Chrysomelidae: Leptinotarsa decemlineata, Diabrotica virgifera, Phaedon brassicae, Phyllotreta striolata*, etc.,
Brentidae: Cylas formicarius, etc.,
Curculionidae: *Hypera postica, Listroderes costirostris, Euscepes* postfasciatus, etc.,
Erirhimidae: *Echinocnemus bipunctatus, Lissorhoptrus oryzophilus*, etc.,
Rhynchophoridae: *Sitophilus zeamais, Sphenophrus venatus*, etc.,
Limnoriidae: *Tomicus piniperda*, etc.,
Platypodidae: Crossotarsus niponicus, etc.,
Lyctidae: *Lyctus brunneus*, etc.
As the Diptera pest, there can be mentioned, for example,
Tipulidae: Tipila aino, etc.,
Bibionidae: Plecia nearctica, etc.,
Fungivoridae: Exechia shiitakevora, etc.,
Lycoriidae: Pnyxiascabiei, etc., Cecidomyiidae: *Asphondylia yusimai, Mayetiola* destructor, etc.,
Culicidae: *Aedes aegypti, Culex* pipiens pallens, etc.,
Simuliidae: Simulim takahasii, etc.,
Chironomidae: *Chironomus* oryzae, etc.,
Tabanidae: *Chrysops suavis, Tabanus trigonus*, etc.,
Syrphidae: Eumerus strigatus, etc.,
Trypetidae: *Bactrocera dorsalis, Euphranta japonia, Ceratitis capitata*, etc.,
Agromyzidae: *Liriomyza trifolii, Chromatomyia horticola*, etc.,
Chloropidae: *Meromyza* nigriventris, etc.,
Drosophilidae: *Drosophila suzukii, Drosophila* melanogaster, etc.,
Ephydridae: *Hydrellia griseola*, etc.,
Hippoboscidae: Hippobosca equina, etc.,
Scatophagidae: Parallelpmma sasakawae, etc.,
Anthomyiidae: *Delia antiqua, Delia platura*, etc.,
Fanniidae: Fannia canicularis, etc.,
Muscidae: *Musca domestica, Stomoxys* calcitrans, etc.,
Sarcophagidae: *Sarcophaga* peregrina, etc.,
Gasterophilidae: Gasterophilus intestinalis, etc.,
Hypodermatidae: *Hypoderma* lineatum, etc.,
Oestridae: Oestrus ovis, etc.
As the Lepidoptera pest, there can be mentioned, for example,
Hepialidae: Endoclita excrescens, etc.,
Heliozelidae: Antispila ampelopsia, etc.,
Cossidae: Zeuzera leuconotum, etc.,
Tortricidae: *Archips fuscocupreanus, Adoxophyes orana fasciata, Grapholita molesta, Homona magnanima, Leguminivora glycinivorella, Cydia* pomenella, etc.,
Cochylidae: *Eupoecilia ambiguella*, etc.,
Psychidae: *Bambalina* sp., *Eumeta minuscula*, etc.,
Tineidae: *Nemapogon granella, Tinea translucens*, etc.,
Nepticulidae: *Bucculatrix pyrivorella*, etc.,
Lyonetiidae: Lyonetia clerkella, etc.,
Gracilariidae: *Caloptilia theivora, Phyllonorycter* ringoniella, etc.,
Phyllocnistidae: Phyllocnistis citrella, etc.,
Acrolepiidae: Acrolepiopsis sapporensis, etc.,
Yponomeutidae: *Plutella xylostella, Yponomeuta* orientalis, etc.,
Argyresthidae: Argyresthia conjugella, etc.,
Aegeriidae: Nokona regalis, etc.,
Gelechiidae: *Phthorimaea operculella, Sitotroga* cerealella, *Pectinophora gossypiella*, etc.,
Carposimidae: *Carposina* sasakii, etc.,
Zygaenidae: *Illiberis* pruni, etc.,
Heterogeneidae: Monema flavescens, etc.,
Crambidae: *Ancylolomia japonica, Chilo suppressalis, Cnaphalocrosis medinalis, Ostrinia furnacalis, Ostrinia* nubilalis, etc.,
Pyralidae: *Cadra cautella, Galleria mellonella*, etc.,
Pterophoridae: *Nippoptilia vitis*, etc.,
Papilionidae: *Papilio xuthus*, etc.,
Pieridae: *Pieris rapae*, etc.,
Hesperiidae: *Parnara guttata* guttata, etc.,
Geometridae: Ascotis selenaria, etc.,
Lasiocampidae: *Dendrolimus* spectabilis, Malacosomaneustrium testaceum, etc.,
Sphingidae: Agrius convolvuli, etc.,
Lymantriidae: *Arna pseudoconspersa, Lymantria dispar*, etc.,
Arctiidae: *Hyphantria cunea*, etc.,
Noctuidae: *Agrotis ipsilon, Autographa nigrisigna, Helicoverpa armigera, Helicoverpa zea, Heliothis virescens, Spodoptera exigua, Spodoptera litura*, etc.

As the Hymenoptera pest, there can be mentioned, for exmaple,

Argidae: Arge pagana, etc.,
Tenthredimidae: Apethymus kuri, Athaliarosae ruficornis, etc.,
Cynipidae: Dryocosmus kuriphilus, etc.,
Vespidae: Vespa simillima xanthoptera, etc.,
Formicidae: *Solenopsis* invicta, etc.,
Megachilidae: Megachile nipponica, etc.

As the Order Collembola pest, there can be mentioned, for example,

Sminthuridae: Bourletiellahortensis, etc.

As the Order Thysanura pest, there can be mentioned, for example,

Lepismatidae: Lepisma saccharina, Ctenolepisma villosa, etc.

As the Blattodea pest, there can be mentioned, for example,

Blattidae: *Periplaneta americana,*
Blattellidae: *Blattella germanica*, etc.

As the Order Isoptera pest, there can be mentioned, for example,

*Kalotermitidae: Incisitermes* minor, etc.,
*Rhinotermitidae: Coptotermes formosanus*, etc.,
*Termitidae: Odontotermes formosanus*, etc.

As the Order Psocoptera pest, there can be mentioned, for example,

Trogiidae: Trogium pulsatorium, etc.,
Liposcelidaidae: Liposcelis corrodens, etc.

As the Order Mallophaga pest, there can be mentioned, for example,

Menoponidae: Lipeurus caponis, etc.,
Trichodectidae: *Damalinia* bovis, etc.

As the Order Anoplura pest, there can be mentioned, for example,

Haematopimidae: Haematopinus suis, etc.,
Pediculine: Pediculus humanus, etc.,
Linognathidae: *Linognathus* setosus, etc.,
Pthiridae: public louse, etc.

As the Plant-feeding mites, there can be mentioned, for example,

Eupodidae: Penthaleus major, etc.,
Tarsonemidae: *Phytonemus pallidus, Polyphagotarsonemus latus*, etc.,
Pyemotidae: *Siteroptes* sp., etc.,
Tenuipalpidae: *Brevipalpus* lewisi, etc.,
Tuckerellidae: Tuckerella pavoniformis, etc.,
Tetranychidae: Eotetranychusboreus, *Panonychus citri, Panonychus ulmi, Tetranychus urticae, Tetranychus kanzawai*, etc.,
Nalepellidae: Trisetacus pini, etc.,
Eriophyidae: *Aculops pelekassi, Epitrimerus pyri, Phyllocoptruta* oleivola, etc.,
Diptilomiopidae: Diptacus crenatae, etc.,
Acaridae: Aleuroglyphus ovatus, Tyrophagus putrescentiae, Rhizoglyphus robini, etc.

As the Plant-parasitic nematodes, there can be mentioned, for example,

Longidoridae: *Xiphinema index*, etc.,
Trichodoridae: *Paratrichodorus minor*, etc.,
Rhabditidae: *Rhabditella* sp., etc.,
Tylenchidae: *Aglenchus*sp., etc.,
Tylodoridae: *Cephalenchus* sp., etc.,
Anguinidae: *Nothotylenchus acris, Ditylenchus destructor*, etc.,
Hoplolaimidae: *Rotylenchulus reniformis, Helicotylenchus dihystera*, etc.,
Paratylenchidae: *Paratylenchus curvitatus*, etc., Meloidogynidae: *Meloidogyne incognita, Meloidogyne hapla*, etc.,
Heteroderidae: *Globodera rostochiensis, Heterodera glycines*, etc.,
Telotylenchidae: *Tylenchorhynchus claytoni* etc.,
Psilenchidae: *Psilenchus* sp., etc.,
Criconematidae: *Criconemoides* sp., etc.,
Tylenchulidae: *Tylenchulus semipenetrans*, etc.,
Sphaeronematidae: *Sphaeronema camelliae*, etc.,
Pratylenchidae: *Radopholus citrophilus, Radopholus similis, Nacobbus aberrans, Pratylenchus penetrans, Pratylenchus coffeae*, etc.,
Iotonchiidae: *Iotonchium ungulatum*, etc.,
Aphelenchidae: *Aphelenchus avenae*, etc.,
Aphelenchoididae: *Aphelenchoides besseyi, Aphelenchoides fragariae*, etc.,
Palasitaphelenchidae: *Bursaphelenchus xylophilus*, etc.

As the plant parasitic mollusc pests, there can be mentioned, for example,

Pilidae: Pomacea canaliculata, etc.,
Veronicellidae: Leavicaulis alte, etc.,
Achatimidae: Achatina fulica, etc.,
Philomycidae: Meghimatium bilineatum, etc.,
Succineidae: Succinealauta, etc.,
Didcidae: Discus pauper, etc.,
Zonitidae: Zonitoides yessoensis, etc.,
Limacidae: *Limax flavus, Deroceras reticulatum*, etc.,
Hehelicarionidae: Parakaliella harimensis, etc.,
Bradybaenidae: Acusta despecta sieboldiana, Bradybaena similaris, etc.

As other pests such as injurious animals, uncomfortable animals, sanitary insects, livestock insects, parasites and the like, there can be mentioned, for example, Acari Macronysshidae: *Ornithonyssus sylvialum*, etc.,
Varroidae: *Varroa jacobsoni*, etc.,
Dermanyssidae: *Dermanyssus gallinae*, etc.,
Macronyssidae: *Ornithonyssus sylvialum*, etc.,
Ixodidae: *Boophilus microplus, Rhipicephalus sanguineus, Haemaphysalis longicornis*, etc.,
Sarcoptidae: *Sarcoptes scabiei*, etc.,
Isopoda Armadillididae: *Armadillidium vulgare*, etc.,
Decapoda Astacidae: *Procambarus clarkii*, etc.,
Porcellionidae: *Porcellionides pruinosus*, etc.,
Chilopoda pests: *Scutigeromorpha Sutigeridae Thereuonema tuberculata, Scolopendromorpha Scolopendra subpinipes* etc.,
Diplopoda pests: *Polydesmida Paradoxosomatidae, Oxidus gracilis* etc.,
*AraneaeLatrodectus hasseltii: Theridiiadae hasseltii*, etc.,
Clubionidae: *Chiracanthium japonicum*, etc.,
Order Scorpionida: *Androctonus crassicauda*, etc.,
Parasitic roundworm: *Ascaris lumbricoides, Syphacia* sp., *Wucherebia bancrofti*, etc.,
Parasitic flatworm: *Distomum* sp., *Paragonimus westermanii, Metagonimus yokokawai, Schistosoma japonicum, Taenia solium, Taeniarhynchus saginatus, Echinococcus* sp., *Diphyllobothrium latum*, etc.

The pest control agent of the present invention exhibits a control effect also to the above-mentioned pests, etc. which already have resistances to existing pest control agents. Further, the present pest control agent can be applied to plants which already have resistances to insects, diseases, herbicides, etc., owing to genetic recombination, artificial mating, etc.

Next, there are described the production methods, formulation methods and applications of the present compound, in detail by way of Examples. However, the present invention is in no way restricted by these Examples.

EXAMPLES

Example 1

Production of 3-amino-2,3-bis(isopropoxyimino)propionitrile (compound No. 1-096)

(1) 2.52 g (14.8 mM) of 2-iodopropane was added to an N,N-dimethylformamide solution (30 ml) of 2.00 g (15.6 mM) of 3-amino-2,3-bis(hydroxyimino)propionitrile. The mixture was cooled to 0° C. 2.05 g (14.8 mM) of potassium carbonate was added, followed by stirring at room temperature for 16 hours. The reaction mixture was poured into water, followed by extraction with ethyl acetate. The organic layer obtained was washed with a saturated aqueous sodium chloride solution, dried over anhydrous magnesium sulfate, and filtered to remove inorganic matter. The solvent was distilled off under reduced pressure. The resulting residue was purified by silica gel column chromatography (ethyl acetete:hexane=1:2) to obtain 1.36 g (yield: 51%) of 3-amino-3-hydroxyimino-2-isopropoxyiminopropionitrile (compound No. 1-004).

$^1$H-NMR data (CDCl$_3$/TMS δ (ppm)):

1.38 (6H, d), 4.63 (1H, sept), 5.02 (2H, bs), 8.54 (1H, bs)

Incidentally, the 3-amino-2,3-bis(hydroxyimino)propionitrile was produced based on the method described in Journal of Organic Chemistry, 2000, Vol. 65, No. 4, pp. 11391143.

(2) 1.35 g (30.9 mM) of 55% sodium hydride was suspended in 20 ml of N,N-dimethylformamide. Thereinto was dropwise added, in ice-cooling, an N,N-dimethylformamide solution (10 ml) of 5.00 g (29.4 mM) of the 3-amino-3-hydroxyimino-2-isopropoxyiminopropionitrile obtained in (1). Stirring was conducted at room temperature for 15 minutes. Thereinto was dropwise added, in ice-cooling, 3.98 g (32.4 mM) of isopropyl bromide. Stirring was conducted at room temperature for 2 hours. The reaction mixture was poured into water. Extraction with ethyl acetate was conducted. The organic layer obtained was washed with a saturated aqueous sodium chloride solution, dried over anhydrous magnesium sulfate, and filtered to remove inorganic matter. The solvent was distilled off under reduced pressure. The resulting residue was purified by silica gel column chromatography (ethyl acetate:hexane=1:4) to obtain 6.12 g (yield: 98%) of the title compound.

$^1$H-NMR data (CDCl$_3$/TMS δ (ppm)):

1.28 (6H, d), 1.36 (6H, d), 4.41 (1H, sept), 4.60 (1H, sept), 4.81 (2H, bs)

Example 2

Production of 3-amino-2-isopropoxyimino-3-propoxyiminopropionitrile (compound No.: 1-073)

To an N—N-dimethylformamide solution (16 ml) of 1.36 g (7.99 mM) of the 3-amino-3-hydroxyimino-2-isopropoxyiminopropionitrile obtained in (1) of Example 1 was added 1.09 g (8.86 mM) of 1-bromopropane. The mixture was cooled to 0° C. Thereto was added 0.35 g (8.0 mM) of 55% sodium hydride. Stirring was conducted at room temperature for 3 hours. The reaction mixture was poured into water. Extraction with ethyl acetate was conducted. The organic layer obtained was washed with a saturated aqueous sodium chloride solution, dried over anhydrous magnesium sulfate, and filtered to remove inorganic matter. The solvent was distilled off under reduced pressure. The resulting residue was purified by silica gel column chromatography (ethyl acetate:hexane=1:2) to obtain 1.61 g (yield: 95%) of the title compound.

$^1$H-NMR data (CDCl$_3$/TMS δ (ppm)):

0.95 (3H, t), 1.36 (6H, d), 1.37-1.77 (2H, m), 4.10 (2H, t), 4.60 (1H, sept), 4.84 (2H, bs)

Example 3

Production of 3-Amino-2,3-Bis(Propoxyimino)Propionitrile (compound No. 1-072)

7.2 g (58.6 mM) of 1-bromopropane was added to an N,N-dimethylformamide solution (50 ml) of 3.00 g (23.4 mM) of 3-amino-2,3-bis(hydroxyimino)propionitrile. The mixture was cooled to 0° C. 22.0 g (159 mM) of potassium carbonate was added. Stirring was conducted at 90° C. for 3 hours. The reaction mixture was returned to room temperature and poured into water. The mixture was subjected to extraction with ethyl acetate. The organic layer obtained was washed with a saturated aqueous sodium chloride solution, dried over anhydrous magnesium sulfate, and filtered to remove inorganic matter. The solvent was distilled off under reduced pressure. The resulting residue was purified by silica gel column chromatography (ethyl acetate:hexane=1:2) to obtain 2.54 g (yield: 51%) of the title compound.

$^1$H-NMR data (CDCl$_3$/TMS δ (ppm)):

0.93-1.01 (6H, m), 1.67-1.84 (4H, m), 4.11 (2H, t), 4.31 (2H, t), 4.83 (2H, bs)

Example 4

Production of 3-amino-2,3-bis(2,2,2-trifluoroethoxyimino)propionitrile (compound No. 1-168)

1.81 g (7.81 mM) of 2,2,2-trifluoroethyl trifluoromethanesulfonate was added to an N,N-dimethylformamide solution (20 ml) of 1.00 g (7.81 mM) of 3-amino-2,3-bis(hydroxyimino)propionitrile. The mixture was cooled to 0° C. Thereto was added 1.08 g (7.81 M) of potassium carbonate. Stirring was conducted at room temperature for 3 hours. The mixture was cooled to 0° C. Thereto were added 1.81 g (7.81 mM) of 2,2,2-trifluoroethyl trifluoromethanesulfonate and 0.34 g (7.8 mM) of 55% sodium hydride. Stirring was conducted at room temperature for 2 hours. The reaction mixture was poured into water. Extraction with ethyl acetate was conducted. The organic layer obtained was washed with a saturated aqueous sodium chloride solution, dried over anhydrous magnesium sulfonate, and filtered to remove inorganic matter. The solvent was distilled off under reduced pressure. The resulting residue was purified by silica gel column chromatography (ethyl acetate:hexane=1:2) to obtain 1.51 g (yield: 66%) of the title compound.

$^1$H-NMR data (CDCl$_3$/TMS δ (ppm)):

4.52 (2H, q), 4.70 (2H, q), 4.99 (2H, bs)

Example 5

Production of 3-amino-3-hydroxyimino-2-isopropoxyiminopropanamide (compound No. 2-004)

To a mixed solution of methanol (1.5 ml) and dimethyl sulfoxide (0.5 ml), of 0.50 g (2.94 mM) of the 3-amino-3-hydroxyimino-2-isopropoxyiminopropionitrile obtained in (1) of Example 1 were added, at room temperature, 0.73 g (6.4 mM) of a 30% aqueous hydrogen peroxide solution and 0.02 g (0.14 mM) of potassium carbonate. Stirring was conducted at room temperature for 4 hours. Excessive hydrogen peroxide was treated with an aqueous sodium thiosulfate solution. The solvent was distilled off under reduced pressure. Water was added to the residue and extraction with ethyl acetate was conducted. The organic layer was washed with a saturated aqueous sodium chloride solution, dried over anhydrous magnesium sulfate, and filtered to remove inorganic matter. The solvent was distilled off under reduced pressure. The resulting crude crystal was washed with a 1:2 mixed solution of diisopropyl ether and n-hexane to obtain 0.35 g (yield: 63%) of the title compound.

$^1$H-NMR data (CDCl$_3$/TMS δ (ppm)): 1.29 (6H, d), 4.43 (1H, sept), 4.88 (2H, bs), 6.73 (2H, bs), 10.20 (1H, bs)

Example 6

Production of 3-amino-2,3-bis(isopropoxyimino)propanamide (compound No. 2-096)

To a methanol solution (140 ml) of 29.0 g (137 mM) of 3-amino-2,3-bis(isopropoxyimino)propionitrile were added, at room temperature, 47 g (415 mM) of a 30% aqueous hydrogen peroxide solution, 1.5 g (15 mM) of sodium carbonate and 2.3 g (7.1 mM) of tetrabutylammonium bromide. Stirring was conducted at room temperature for 4 hours. Since the raw materials remained, further 24 g (212 mM) of a 30% aqueous hydrogen peroxide solution was added, followed by stirring at room temperature for 3 hours. Excessive hydrogen peroxide was treated with an aqueous sodium thiosulfate solution. The solvent was distilled off under reduced pressure. Water was added to the resulting residue, followed by extraction with ethyl acetate. The organic layer obtained was washed with a saturated aqueous sodium chloride solution, dried over anhydrous magnesium sulfate, and filtered to remove inorganic matter. The solvent was distilled off under reduced pressure. The crystal obtained was washed with a 1:2 mixed solution of diisopropyl ether and n-hexane to obtain 29.0 g (yield: 92%) of the title compound.

$^1$H-NMR data (CDCl$_3$/TMS δ (ppm)):
1.24 (6H, d), 1.29 (6H, d), 4.34 (1H, sept), 4.45 (1H, sept), 4.78 (2H, bs), 5.71 (2H, bs)

Other glyoxime derivatives were produced based on the above Examples, and their structural formulas and properties are shown in Table 13 to Table 15 together with those of the compounds produced in the above Examples. In these tables, symbols have the same meanings as shown previously. Incidentally, compound Nos. are referred in the later description.

TABLE 13

| Compound No. | Physical Property | |
|---|---|---|
| 1-001 | Melting Point (° C.) | 176-179 |
| 1-002 | Melting Point (° C.) | 136-139 |
| 1-003 | Melting Point (° C.) | 110-113 |
| 1-004 | Melting Point (° C.) | 155-157 |
| 1-005 | Melting Point (° C.) | 106-108 |
| 1-006 | Melting Point (° C.) | 135-138 |
| 1-007 | Melting Point (° C.) | 153-155 |
| 1-010 | Melting Point (° C.) | 129-132 |
| 1-013 | Melting Point (° C.) | 157-160 |
| 1-014 | Melting Point (° C.) | 107-109 |
| 1-016 | Melting Point (° C.) | 151-153 |
| 1-018 | Melting Point (° C.) | 120-121 |

TABLE 13-continued

| Compound No. | Physical Property | |
|---|---|---|
| 1-021 | Melting Point (° C.) | 123-124 |
| 1-022 | Melting Point (° C.) | 170-173 |
| 1-041 | Reflective Index ($n_D^{20}$) | 1.5215 |
| 1-051 | Reflective Index ($n_D^{20}$) | 1.4975 |
| 1-070 | Reflective Index ($n_D^{20}$) | 1.5101 |
| 1-071 | Reflective Index ($n_D^{20}$) | 1.5025 |
| 1-072 | Reflective Index ($n_D^{20}$) | 1.4974 |
| 1-073 | Reflective Index ($n_D^{20}$) | 1.4973 |
| 1-074 | Reflective Index ($n_D^{20}$) | 1.4960 |
| 1-075 | Reflective Index ($n_D^{20}$) | 1.4940 |
| 1-076 | Reflective Index ($n_D^{20}$) | 1.4960 |
| 1-079 | Reflective Index ($n_D^{20}$) | 1.4910 |
| 1-082 | Reflective Index ($n_D^{20}$) | 1.4950 |
| 1-084 | Reflective Index ($n_D^{20}$) | 1.4875 |
| 1-085 | Reflective Index ($n_D^{20}$) | 1.5175 |
| 1-087 | Reflective Index ($n_D^{20}$) | 1.5144 |
| 1-090 | Reflective Index ($n_D^{20}$) | 1.5123 |

TABLE 14

| Compound No. | Physical Property | |
|---|---|---|
| 1-091 | Reflective Index ($n_D^{20}$) | 1.5220 |
| 1-092 | Reflective Index ($n_D^{20}$) | 1.5242 |
| 1-094 | Reflective Index ($n_D^{20}$) | 1.4982 |
| 1-096 | Reflective Index ($n_D^{20}$) | 1.4937 |
| 1-098 | Reflective Index ($n_D^{20}$) | 1.4870 |
| 1-107 | Reflective Index ($n_D^{20}$) | 1.4886 |
| 1-110 | Reflective Index ($n_D^{20}$) | 1.5082 |
| 1-116 | Reflective Index ($n_D^{20}$) | 1.4910 |
| 1-117 | Reflective Index ($n_D^{20}$) | 1.4890 |
| 1-118 | Reflective Index ($n_D^{20}$) | 1.5108 |
| 1-119 | Reflective Index ($n_D^{20}$) | 1.4520 |
| 1-121 | Reflective Index ($n_D^{20}$) | 1.5090 |
| 1-122 | Reflective Index ($n_D^{20}$) | 1.5140 |
| 1-123 | Reflective Index ($n_D^{20}$) | 1.4873 |
| 1-124 | Reflective Index ($n_D^{20}$) | 1.4925 |
| 1-125 | Reflective Index ($n_D^{20}$) | 1.5100 |
| 1-126 | Reflective Index ($n_D^{20}$) | 1.5225 |
| 1-127 | Reflective Index ($n_D^{20}$) | 1.4902 |
| 1-128 | Reflective Index ($n_D^{20}$) | 1.4890 |
| 1-129 | Reflective Index ($n_D^{20}$) | 1.5010 |
| 1-130 | Reflective Index ($n_D^{20}$) | 1.4980 |
| 1-131 | Melting Point (° C.) | 72-74 |
| 1-132 | Reflective Index ($n_D^{20}$) | 1.5075 |
| 1-133 | Reflective Index ($n_D^{20}$) | 1.5250 |
| 1-134 | Reflective Index ($n_D^{20}$) | 1.5273 |
| 1-135 | Reflective Index ($n_D^{20}$) | 1.5270 |
| 1-136 | Reflective Index ($n_D^{20}$) | 1.4372 |
| 1-137 | Reflective Index ($n_D^{20}$) | 1.4905 |
| 1-138 | Melting Point (° C.) | 164-167 |

TABLE 15

| Compound No. | Physical Property | |
|---|---|---|
| 1-140 | Melting Point (° C.) | 99-101 |
| 1-141 | Melting Point (° C.) | 173-176 |
| 1-142 | Reflective Index ($n_D^{20}$) | 1.5140 |
| 1-143 | Melting Point (° C.) | 54-55 |
| 1-144 | Reflective Index ($n_D^{20}$) | 1.4940 |
| 1-147 | Melting Point (° C.) | 73-76 |
| 1-148 | Reflective Index ($n_D^{20}$) | 1.5551 |
| 1-149 | Reflective Index ($n_D^{20}$) | 1.5501 |
| 1-154 | Melting Point (° C.) | 124-127 |
| 1-155 | Reflective Index ($n_D^{20}$) | 1.5122 |
| 1-157 | Reflective Index ($n_D^{20}$) | 1.5043 |
| 1-159 | Reflective Index ($n_D^{20}$) | 1.5660 |
| 1-160 | Reflective Index ($n_D^{20}$) | 1.5141 |
| 1-161 | Reflective Index ($n_D^{20}$) | 1.5750 |

TABLE 15-continued

| Compound No. | Physical Property | |
| --- | --- | --- |
| 1-162 | Reflective Index ($n_D^{20}$) | 1.4402 |
| 1-164 | Melting Point (° C.) | 81-83 |
| 1-165 | Melting Point (° C.) | 76-79 |
| 2-004 | Melting Point (° C.) | 161-164 |
| 2-051 | Melting Point (° C.) | 106-107 |
| 2-072 | Melting Point (° C.) | 66-69 |
| 2-096 | Melting Point (° C.) | 157-160 |
| 2-116 | Melting Point (° C.) | 140-143 |

With respect to compound Nos. 1-120, 1-139, 1-156, 1-158 and 1-163, their $^1$H-NMR data (CDCl$_3$/TMS δ (ppm)) are shown below.

Compound No. 1-120: 1.22 (3H, t), 1.38 (6H, d), 3.54 (2H, q), 3.73 (2H, t), 4.29 (2H, t), 4.61 (1H, sept), 4.94 (2H, s)

Compound No. 1-139: 0.95 (3H, t), 1.67-1.79 (2H, m), 4.13 (2H, t), 4.68 (2H, q), 4.83 (2H, bs)

Compound No. 1-156: 0.94 (3H, t), 1.35-1.45 (2H, m), 1.65-1.72 (2H, m), 4.16 (2H, t), 4.83 (2H, d), 4.83 (2H, bs), 5.32-5.40 (2H, m), 5.95-6.05 (1H, m)

Compound No. 1-158: 0.89 (3H, t), 1.24-1.32 (6H, m), 1.65-1.71 (2H, m), 4.14 (2H, t), 4.83 (2H, d), 4.83 (2H, bs), 5.31-5.41 (2H, m), 5.93-6.06 (1H, m)

Compound No. 1-163: 1.29 (6H, d), 4.43 (1H, sept), 4.74-4.80 (4H, m)

Next, there are specifically explained examples of formulating the present pest control agent by using the present glyoxime derivative produced as above or its agriculturally acceptable salt. Incidentally, the kinds and proportions of compounds and additives used in each formulation are not restricted to those shown in the following formation examples and may be varied in a wide range. In the following explanation, part or parts refer to mass part or mass parts.

Formulation Example 1 Emulsifiable Concentrate

| A compound described in Table 1 to Table 12 | 10 parts |
| --- | --- |
| Cyclohexanone | 30 parts |
| Polyoxyethylene alkyl aryl ether | 11 parts |
| Calcium alkylbenzenesulfonate | 4 parts |
| Methylnaphthalene | 45 parts |

The above materials were made into a uniform solution, to prepare an emulsifiable concentrate.

Formulation Example 2 Wettable Powder

| A compound described in Table 1 to Table 12 | 10 parts |
| --- | --- |
| Sodium salt of naphthalenesulfonic acid-formalin Condensate | 0.5 part |
| Polyoxyethylene alkyl aryl ether | 0.5 part |
| Diatomaceous earth | 24 parts |
| Clay | 65 parts |

The above materials were mixed and ground to prepare a wettable powder.

Formulation Example 3 Powder

| A compound described in Table 1 to Table 12 | 2 parts |
| --- | --- |
| Diatomaceous earth | 5 parts |
| Clay | 93 parts |

The above materials were mixed and ground to prepare a powder.

Formulation Example 4 Granule

| A compound described in Table 1 to Table 12 | 5 parts |
| --- | --- |
| Sodium salt of lauryl alcohol sulfate | 2 parts |
| Sodium ligninsulfonate | 5 parts |
| Carboxymethyl cellulose | 2 parts |
| Clay | 86 parts |

The above materials were mixed and ground. Thereto was added 20 parts of water, followed by kneading. The kneaded material was passed through an extrusion granulator to obtain granules of 14 to 32 meshes. The granules were dried to prepare a granule.

Next, the effect of the pest control agent of the present invention is shown by Test Examples.

Test Example 1

Insecticidal action test for *Nilaparvata lugens* Stål (Brown Rice Planthopper) (Immersion Test)

A wettable powder prepared based on Formulation Example 2 was diluted with water so that the concentration of active ingredient became 500 ppm. In the diluted liquid was immersed sprouting unhulled rice. The immersed rice was placed in a plastic cup of 60 ml. Into the plastic cup were released 10 2-age larvae of *Nilaparvata lugens* Stål (brown rice planthopper). The cup was covered with a cap and placed in a thermostat of 25° C. After 6 days, the number of living insects was counted and the mortality of insect was calculated using the calculation formula of Mathematical Expression 1. This test was conducted with no repetition.

Insect mortality(%)=[1−(number of living insects)/(number of tested insects)]×100      [Mathematical Expression 1]

The compound Nos. of the compounds which gave an insect mortality of 90% or higher in the above test, are shown below.

1-004, 1-018, 1-041, 1-051, 1-070, 1-071, 1-072, 1-073, 1-074, 1-075, 1-076, 1-079, 1-082, 1-084, 1-085, 1-087, 1-090, 1-091, 1-092, 1-094, 1-096, 1-098, 1-107, 1-110, 1-116, 1-117, 1-118, 1-119, 1-121, 1-122, 1-123, 1-124, 1-127, 1-128, 1-129, 1-130, 1-133, 1-134, 1-135, 1-136, 1-137, 1-139, 1-142, 1-143, 1-144, 1-147, 1-155, 1-156, 1-157, 1-160, 1-162, 1-163

Test Example 2

Insecticidal Action Test for *Plutella xylostella* Linné(Diamondback Moth) (Immersion Test)

A wettable powder prepared based on Formulation Example 2 was diluted with water so that the concentration of active ingredient became 500 ppm. In the diluted formulation were immersed cabbage leaves. The resulting cabbage leaves were placed in a plastic cup of 60 ml. Into the plastic cup were released 10 2-age larvae of *Plutella xylostella* Linné(diamondback moth). The plastic cup was covered with a cap and placed in a thermostat of 25° C. After 6 days, the number of living insects was counted and the mortality of insect was calculated using the calculation formula of Mathematical Expression 1. This test was conducted with no repetition.

The compound Nos. of the compounds which gave an insect mortality of 90% or higher in the above test, are shown below.

1-005, 1-076, 1-090, 1-091, 1-117, 1-121, 1-122, 1-124, 1-128, 1-156

The invention claimed is:

1. A pest control agent comprising as an active ingredient, a glyoxime derivative represented by the general formula

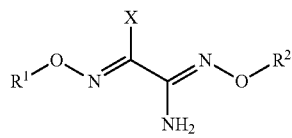

[I]

wherein X is a cyano group or a carbamoyl group,
$R^1$ is a $C_1$~$C_8$ alkyl group, a $C_2$~$C_6$ alkenyl group, a $C_2$~$C_6$ alkynyl group, a $C_3$~$C_6$ cycloalkyl group, a $C_3$~$C_6$ cycloalkyl $C_1$~$C_6$ alkyl group, a $C_1$~$C_6$ haloalkyl group, a $C_1$~$C_6$ alkoxy $C_1$~$C_6$ alkyl group, a cyano $C_1$~$C_6$ alkyl group or a phenyl $C_1$~$C_6$ alkyl group which may be substituted by at least one substituent selected from a substituent group α, which consists of a halogen atom, a $C_1$~$C_6$ alkyl group, a $C_1$~$C_6$ haloalkyl group, a $C_1$~$C_6$ alkoxy group, a $C_1$~$C_6$ haloalkoxy group, a nitro group or a cyano group,
$R^2$ is a hydrogen atom, a $C_1$~$C_8$ alkyl group, a $C_2$~$C_6$ alkenyl group, a $C_2$~$C_6$ alkynyl group, a $C_3$~$C_6$ cycloalkyl group, a $C_3$~$C_6$ cycloalkyl $C_1$~$C_6$ alkyl group, a $C_1$~$C_6$ haloalkyl group, a $C_1$~$C_6$ alkoxy $C_1$~$C_6$ alkyl group, a cyano $C_1$~$C_6$ alkyl group or a phenyl $C_1$~$C_6$ alkyl group which may be substituted by at least one substituent selected from a substituent group α,
or an agriculturally acceptable salt thereof.

2. A glyoxime derivative represented by the general formula

[I']

wherein X' is a cyano group or a carbamoyl group,
$R^{1'}$ is a $C_3$~$C_8$ alkyl group, a $C_2$~$C_6$ alkenyl group, a $C_2$~$C_6$ alkynyl group, a $C_3$~$C_6$ cycloalkyl group, a $C_3$~$C_6$ cycloalkyl $C_1$~$C_6$ alkyl group, a $C_2$~$C_6$ haloalkyl group, a $C_1$~$C_6$ alkoxy $C_1$~$C_6$ alkyl group, a cyano $C_1$~$C_6$ alkyl group or a phenyl $C_1$~$C_6$ alkyl group which may be substituted by at least one substituent selected from a substituent group α, which consists of a halogen atom, a $C_1$~$C_6$ alkyl group, a $C_1$~$C_6$ haloalkyl group, a $C_1$~$C_6$ alkoxy group, a $C_1$~$C_6$ haloalkoxy group, a nitro group or a cyano group,
$R^{2'}$ is a hydrogen atom, a $C_1$~$C_8$ alkyl group, a $C_2$~$C_6$ alkenyl group, a $C_2$~$C_6$ alkynyl group, a $C_3$~$C_6$ cycloalkyl group, a $C_3$~$C_6$ cycloalkyl $C_1$~$C_6$ alkyl group, a $C_1$~$C_6$ haloalkyl group, a $C_1$~$C_6$ alkoxy $C_1$~$C_6$ alkyl group, a cyano $C_1$~$C_6$ alkyl group or a phenyl $C_1$~$C_6$ alkyl group which may be substituted by at least one substituent selected from the substituent group α,
or an agriculturally acceptable salt thereof.

3. A pest control agent according to claim 1, which is an insecticide.

4. A method for pest control which uses the glyoxime derivative or agriculturally acceptable salt thereof, according to claim 2, at an effective amount.

5. A method for pest control according to claim 4, which uses the glyoxime derivative or agriculturally acceptable salt thereof, as an insecticide.

* * * * *